US010632182B2

(12) United States Patent
Genin et al.

(10) Patent No.: US 10,632,182 B2
(45) Date of Patent: Apr. 28, 2020

(54) METHODS FOR FREEZE-DRYING AND REHYDRATING BIOLOGICS

(71) Applicants: BOEHRINGER INGELHEIM ANIMAL HEALTH USA INC., Duluth, GA (US); VITAMFERO SA, Angers (FR); L'Universite De Bourgogne, Dijon (FR); L'Institut National Superieur des Sciences Agronomiques de L'Alimentation et de L'Environment, Dijon (FR)

(72) Inventors: Noel Yves Henri Jean Genin, Saint Genis les Ollieres (FR); Jean-Christophe Audonnet, Lyons (FR); Didier Roy, Combs-la-Ville (FR); Edouard Seche, Orleans (FR); Patrick Gervais, Quetigny (FR); Samira Khaldi-Plassart, Dijon (FR); Romain Useo, Lyons (FR); Joelle DeConinck, Clenay (FR)

( * ) Notice: Subject to any disclaimer, the term of this patent is extended or adjusted under 35 U.S.C. 154(b) by 0 days.

(21) Appl. No.: 15/311,093

(22) PCT Filed: May 13, 2015

(86) PCT No.: PCT/US2015/030588
§ 371 (c)(1),
(2) Date: Nov. 14, 2016

(87) PCT Pub. No.: WO2015/175672
PCT Pub. Date: Nov. 19, 2015

(65) Prior Publication Data
US 2017/0087230 A1    Mar. 30, 2017

(30) Foreign Application Priority Data
May 14, 2014   (EP) .................................. 14168327

(51) Int. Cl.
*A61K 39/002*   (2006.01)
*A01N 1/02*     (2006.01)
*A61K 9/00*     (2006.01)
*A61K 9/19*     (2006.01)
*A61K 39/00*    (2006.01)

(52) U.S. Cl.
CPC .............. *A61K 39/002* (2013.01); *A01N 1/02* (2013.01); *A01N 1/0221* (2013.01); *A01N 1/0278* (2013.01); *A01N 1/0284* (2013.01); *A61K 9/0019* (2013.01); *A61K 9/19* (2013.01); *A61K 2039/522* (2013.01); *Y02A 50/41* (2018.01); *Y02A 50/412* (2018.01)

(58) Field of Classification Search
None
See application file for complete search history.

(56) References Cited

U.S. PATENT DOCUMENTS

2011/0262965 A1* 10/2011 Barrett ................... C12N 5/005
                                                            435/69.1
2012/0039956 A1   2/2012 Harel et al.

FOREIGN PATENT DOCUMENTS

| EP | 2 241 615 A1 | 10/2010 |
| WO | WO 92/14360 | 9/1992 |
| WO | WO 2012/098358 A1 | 7/2012 |

OTHER PUBLICATIONS

Teetor-Barsch et al. Journal of Invertebrate Pathology 33, 300-306, 1979.*
Singh et al. Journal of Biological Sciences 14 (2):95-109, 2014.*
Innes et al. Mem Inst Oswaldo Cruz, Rio de Janeiro, vol. 104(2):246-251, Mar. 2009.*
Mar. 2009; Innes et al. Veterinary Parasitology 180 (2011) 155-163.*
Falcon et al. Veterinary Parasitology 166, 2009 15-20.*
Marcotty T et al. "Lyophilisation and resuscitation of sporozoites of Theileria parva: preliminary experiments", Vaccine, vol. 22, No. 2, Dec. 12, 2003, pp. 213-216.
De Carvalho Vilela et al. "Successful vaccination against Leishmania chagasi infection in BALB/c mice with freeze-thawed Leishmania antigen and Corynebacterium parvum",Acta Tropica, vol. 104, No. 2-3, Oct. 17, 2007, pp. 133-139.
Mitchell G H et al.: "A freeze-dried merozoite vaccine effective against Plasmodium knowlesi malaria", Clinical and Experimental Immunology, vol. 28, 1977, pp. 276-279.
Lu F et al. "The temperature-sensitive mutants of Toxoplasma gondii and ocular toxoplasmosis", Vaccine, vol. 27, No. 4, Jan. 22, 2009, pp. 573-580.
Adams: "Freeze-drying Biological Materials", Drying Technology, v.9, n.4, Sep. 1991, 891-925.
Tang XC et al. "Design of Freeze-Drying Processes for Pharmaceuticals: Practical Advice", Pharmaceutical Research, vol. 21, No. 2, Feb. 2004, pp. 191-200.
Paul Matejtschuk et al: "Freeze-Drying of Biological Standards", Freeze Drying/ Lyophilization of Pharmaceutical and Biological Products, 2010, pp. 317-353.
Sherwood et al. Experimental Cryptosporidiosis in Laboratory Mice. Infection and Immunity, Nov. 1982, p. 471-75. vol. 38, No. 2.
Suzaki et al. "A simplified Freeze-drying Technique for Protozoan Cells." JEM, V27, N2, 153-6.
Harp et al. "Protection of calves with a vaccine against Cryptosporidium parvum." J Parasitol. Feb. 1995;81(1):54-7.

* cited by examiner

*Primary Examiner* — Oluwatosin A Ogunbiyi
(74) *Attorney, Agent, or Firm* — Judy Jarecki-Black; Steffan Finnegan

(57) ABSTRACT

The present invention relates generally to the fields of immunology and vaccine technology. More specifically, the present invention relates to methods for freeze-drying biological preparations, including peptides, antigens, antibodies, and especially, cells. Importantly, the disclosed methods preserve the viability, infectivity and immunogenicity of cells from the Apicomplexa phylum, the Sarcocystidae family, and in particular, cells from the *Toxoplasma* genus.

24 Claims, No Drawings

METHODS FOR FREEZE-DRYING AND REHYDRATING BIOLOGICS

CROSS-REFERENCE TO RELATED APPLICATIONS

This application claims benefit of EP application number EP14168327.6, which was filed 14 May 2014, and which is incorporated herein by reference in its entirety.

INCORPORATION BY REFERENCE

All references cited herein are incorporated by reference in their entirety.

FIELD OF THE INVENTION

The present invention relates generally to the fields of immunology and vaccine technology. More specifically, the present invention relates to methods for freeze-drying and rehydrating immunogenic and/or vaccine compositions that may comprise, inter alia, parasites, including protozoa, including *Toxoplasma* spp. The invention further relates to stabilized, freeze-dried immunogenic and/or vaccine compositions of, for example, *T. gondii*, which may contain these stabilizers. Other aspects of the invention are described in or are obvious from the following disclosure, and are within the ambit of the invention.

BACKGROUND OF THE INVENTION

Lyophilization, or the process of freeze-drying, is a commonly used technique to remove water in the preparation of dehydrated products. Generally, "freeze-drying" an aqueous composition involves three steps. First, the aqueous composition is frozen under conditions of low temperature. Secondly, the frozen water is removed by sublimation under conditions of reduced pressure and low temperature. At this stage, the composition usually contains about 15% water. Third, the residual water is further removed by desorption under conditions of reduced pressure and higher temperatures. At the end of the lyophilization process, a freeze-dried product, also called a "pastille" or "cake" is produced. The freeze-dried product contains very low residual water (from about 0.5% to about 5% weight/weight) and dry material in an amorphous form. This specific state is qualified as "vitreous." Prior to use, the dried products must be rehydrated, which can greatly compromise the integrity of biological structures, especially in the case of whole cells/organisms. But damage to the freeze-dried products, including loss of viability, diminished immunogenicity, and impaired/abolished infectivity, can occur during any of the above-recited steps (i.e. freeze-drying, storage, reconstitution, and post-reconstitution storage). Accordingly, experimentally-determined stabilizers must be added to compositions, prior to subjecting them to lyophilization, and the magnitude and kinetics of each step, particularly the rehydration step, must be precisely defined (Mille et al. (2003) Biotech Bioeng. 83, 578). At the time of this filing, Applicants are aware of no safe and effective stabilizers or freeze-drying methods for preserving the viability, infectivity, and immunogenicity of protozoan parasites, including *T. gondii*, during all phases of the freeze-drying/rehydration process.

Stabilization of biological ingredients in dry form has typically involved the preservation of antitoxins, antigens and bacteria (Flosodort et al (1935) J. Immunol. 29, 389).

However, a limitation in this process included partial denaturation of proteins when dried from an aqueous state at ambient temperatures. Drying from the frozen state helped reduce denaturation and led to better, although incomplete, preservation of biological ingredients including bacteria and viruses (Stamp et al. (1947) J. Gen. Microbiol. 1, 251; Rightsel et al. (1967) Cryobiology 3, 423; Crowe et al. (1971) Cryobiology 8, 251). Nevertheless freezing must be managed in order to maintain an optimal viability of such biological ingredients (Dumont et al. (2004) Appl. Env. Microbiol. 70, 268).

Immunogenic compositions and vaccine compositions comprising biological ingredients, such as viruses, bacteria, parasites, fungi, proteins, polypeptides, glycoproteins, and especially, attenuated live microorganisms, are markedly sensitive to the conditions by which they are prepared, formulated and stored. Such biological ingredients can be modified and degraded by chemical reactions (e.g. hydrolysis, deamination, Maillard's reaction), many of which are mediated by water. Liquid water allows for molecular movements and can result in modification of protein conformations in compositions comprising biological ingredients. By limiting access to water, or by removing water, a major factor of modification and degradation is reduced. This water transfer must be carefully regulated to avoid yeast damages (Gervais et al. (1992) Biotech. Bioeng. 40, 1435). Prior methods to confer stability to biological ingredients have primarily involved freezing the water or removing water by freeze-drying.

More recently, sugars such as sucrose, raffinose and trehalose have been added in various combinations as stabilizers prior to lyophilization of viruses. A large number of compounds have been tested for their ability to stabilize different vaccines containing live attenuated biological ingredients, in particular viruses. Such compounds include SPGA (sucrose, phosphate, glutamate, and albumin; Bovarnick et al. (1950) J. Bacteriol. 59, 509-522; U.S. Pat. No. 4,000,256), bovine or human serum albumin, alkali metal salts of glutamic acid, aluminum salts, sucrose, gelatin, starch, lactose, sorbitol, Tris-EDTA, casein hydrolysate, sodium and potassium lactobionate, and monometallic or dimetallic alkali metal phosphate. Other compounds include, for example, SPG-NZ amine (e.g. U.S. Pat. No. 3,783,098) and polyvinylpyrrolidone (PVP) mixtures (e.g. U.S. Pat. No. 3,915,794). To preserve live attenuated flaviviruses, one group has combined a complex mixture of multiple compounds, including sorbitol, sucrose, optionally trehalose and/or other disaccharide or trisaccharides, urea, and a specific combination of amino acids (U.S. Pat. No. 8,142,795, to Sanofi Pasteur).

As regards preserving still more complicated biological structures, one reference discloses a process for lyophilizing of a mixture of *Anaplasma* (a bacterium), *Toxoplasma* cells, and blood cells (WO 92/14360, to Cryopharm Corporation). This method keeps the parasites viable, but only in the context of their host cells. More recently, WO 2009/099075 (Snow Brand Milk Product Co., Ltd) disclosed a viability-preserving, freeze-drying method for *bifidobacterium, lactobacillus, streptococcus* and *lactococcus*, involving milk components. Even more recently, WO 2012/098358 (Biopharma Technology Ltd) described a method for freeze-drying cell-based biological material while retaining some viability after reconstitution.

REVIEW OF OTHER RELATED LITERATURE REFERENCES

Marcotty et al. "Freeze and resuscitation of sporozoites of *Theileria parva*: preliminary experiments." Vaccine, 22

(2003) 213-216. This reference disclosed the freeze-drying of *Theileria parva* sporozoites and subsequent immunization of cattle against East Coast fever. After injection, several calves exhibited clinical symptoms and development of parasites (schizonts and piroplasms) was observed in biopsies. Only 0.1 to 1% of sporozoites appeared to survive the lyophilization.

Harp et al. "Protection of calves with a vaccine against *Cryptosporidium parvum*." J. Parasitology, Vol. 81, No. 1 (February, 1995), pp. 54. This reference presented data indicating that a vaccine containing freeze-dried oocysts could reduce diarrhea and excretion of oocysts after oral challenge with viable *Cryptosporidium parvum* oocysts. As there did not appear to be an increase in antibody titer (against *C. parvum*), the vaccine's efficacy might be explained by a cellular, but not an humoral immune response. Oocyte viability was destroyed by lyophilization.

Suzaki et al. "A simplified freeze-drying technology for protozoan cells." J. Electron Microsc, Vol. 27, No. 2, 153-156, 1978. Although some superficial preservation was achieved, as indicated by EM, the disclosed lyophilization method failed to preserve viability or infectivity.

Gertrud E and Kramer J. "The Preservation of Infective spores of *Octosporea muscae domesticae* in *Phormia regina*, of *Nosema algerae* in *Anopheles stephensi*, and of *Nosema whitei* in *Tribolium castaneum* by Lyophilization." J. Invertebrate Pathology, 33, 300-306 (1979). Spores of three species of microsporidia (obligate intracellular parasites) were lyophilized "naked," or in host cells. The lyophilisates were then brought into contact with the target animals. The "naked" freeze-dried parasites, formulated in a solution of 50% glucose, were infectious for the target species.

Sherwood et al. "Cryptosporidiosis in Laboratory Experimental Mice." Infection and Immunity, November 1982, p. 471-475. This reference disclosed that freezing and lyophilization failed to preserve the viability of *Cryptosporidium* sp.

Du Plessis et al. "The freeze-drying of *Cowdria ruminantium*." This reference disclosed that lyophilized parasites, within host cells, were infectious in mice and sheep. The precise form/state of the parasites was not evident.

Consequently, there remains a need for new formulation solutions and freeze-drying process for preserving the viability, immunogenicity and infectivity of protozoan parasites—particularly "fragile" and/or "naked" parasites—in freeze-dried form.

Citation or identification of any document in this application is not an admission that such document is available as prior art to the present invention.

SUMMARY OF THE INVENTION

The present invention pertains to a lyophilized composition containing freeze-dried protozoa of intracellular nature, said lyophilized composition being capable of reconstitution to restore said protozoa to viable and infectious states.

A second aspect of the present invention is providing a process for obtaining a lyophilized composition containing freeze-dried protozoa of intracellular nature and being capable of reconstitution to restore said protozoa to viable and infectious states comprising a step of freeze-drying a suspension of protozoa of intracellular nature, devoid of protozoal host cells, in an aqueous formulation solution.

The invention also relates to a rehydrated lyophilized composition comprising a lyophilized composition as defined above in a rehydration medium, wherein said lyophilized composition contains freeze-dried protozoa of intracellular nature, said rehydrated lyophilized composition being such that the protozoa contained in it are viable and infectious.

In one embodiment, the present invention relates to a lyophilized composition containing freeze-dried protozoa of intracellular nature, said lyophilized composition being devoid of protozoal host cells, containing a moisture content of less than 12% by weight and being capable of reconstitution to restore said protozoa to viable and infectious states.

In an advantageous embodiment, the present invention relates to a lyophilized composition as defined above, capable of reconstitution to restore said protozoa to viable and infectious states, said viable protozoa accounting for more than 1% of the freeze-dried protozoa.

In an advantageous embodiment, the present invention relates to a lyophilized composition as defined, being capable of reconstitution to restore said protozoa to viable and infectious states after a storage of said lyophilized composition for a period of time longer than two weeks at a temperature from −25° C. to 25° C., in particular at a temperature from −25° C. to 2° C., at a temperature from 2 to 8° C., more particularly at a temperature from 2 to 6° C., or at a temperature from 8 to 25° C.

In one embodiment, the present invention relates to a lyophilized composition containing freeze-dried protozoa of intracellular nature, said lyophilized composition being devoid of protozoal host cells, containing a moisture content of less than 12% by weight and being capable of reconstitution to restore said protozoa to viable and infectious states, said viable protozoa accounting for more than 1% of the freeze-dried protozoa, in particular after a storage of said lyophilized composition for a period of time longer than two weeks at a temperature from −25° C. to 25° C., in particular at a temperature from −25° C. to 2° C., at a temperature from 2 to 8° C., more particularly at a temperature from 2 to 6° C., or at a temperature from 8 to 25° C.

In an advantageous embodiment, the invention relates to a lyophilized composition as defined above, wherein said freeze-dried protozoa are protozoa of fragile state.

As used herein, "fragile" state protozoa conform to at least one of the following descriptors (i.e. in the absence of suitable protective components and procedures):
  they are obligate intracellular protozoa, which are present outside their host cells, for example, in the extracellular matrix;
  they have a survival rate less than 1% after 15 days when stored in a cell culture medium at 4° C.;
  they lose their infectivity during freezing;
  they lose their infectivity during lyophilization;
  they lose their viability during freezing;
  they lose their viability during lyophilization;
  they are lyophilized parasites that lose their infectivity after 15 days of storage at +4° C.;
  they are lyophilized parasites that lose their viability after 15 days of storage at +4° C.

In an advantageous embodiment, said fragile state is the tachyzoite state, the bradyzoite state, the sporozoite state, the promastigote state, the amastigote state, the epimastigote state or the trypomastigote state.

In another embodiment, said fragile state is the tachyzoite state, the bradyzoite state, the sporozoite state, the promastigote state, the amastigote state, the epimastigote state, the trypomastigote state or the merozoite state.

In one embodiment, the invention relates to a lyophilized composition containing freeze-dried protozoa of intracellular nature, said lyophilized composition being devoid of protozoal host cells, containing a moisture content of less than 12% by weight and being capable of reconstitution to restore said protozoa to viable and infectious states, wherein said freeze-dried protozoa are protozoa of fragile state, in particular of the tachyzoite state, of the bradyzoite state, of the sporozoite state, of the promastigote state, of the amastigote state, of the epimastigote state, of the trypomastigote state or of the merozoite state.

In another embodiment, the invention relates to a lyophilized composition containing freeze-dried protozoa of intracellular nature, said lyophilized composition being devoid of protozoal host cells, containing a moisture content of less than 12% by weight and being capable of reconstitution to restore said protozoa to viable and infectious states, wherein said freeze-dried protozoa are protozoa of fragile state, in particular of the tachyzoite state, of the bradyzoite state, of the sporozoite state, of the promastigote state, of the amastigote state, of the epimastigote state or of the trypomastigote state.

In an advantageous embodiment, the present invention relates to a lyophilized composition as defined above, capable of being stored at a temperature comprised from $-25°$ C. to $10°$ C. for at least 12 months before being reconstituted.

In an advantageous embodiment, the present invention relates to a lyophilized composition as defined above, capable of reconstitution to restore the immunogenic activity of said freeze-dried protozoa.

In an advantageous embodiment, the present invention relates to a lyophilized composition as defined above, capable of reconstitution to restore the prophylactic activity of said freeze-dried protozoa.

In another embodiment, the present invention relates to a lyophilized composition as defined above, wherein the moisture content is less than 11% by weight, less than 10%, less than 9%, less than 8%, less than 7%, less than 6%, less than 5% or less than 4%.

In an advantageous embodiment, the present invention relates to a lyophilized composition as defined above, comprising elements of the culture medium of said protozoa and at least one cryoprotectant.

In another embodiment, the lyophilized composition as defined above, further comprises at least one osmoprotectant and/or at least one antioxidant and/or at least one other additive.

In an advantageous embodiment, the present invention relates to a lyophilized composition as defined above, comprising elements of the culture medium of said protozoa, at least one cryoprotectant, at least one osmoprotectant, at least one antioxidant and/or at least one other additive.

In one embodiment, said culture medium is chosen among DMEM, RPMI or PBS.

In one embodiment, said cryoprotectant is chosen among DMSO, a monosaccharide, a disaccharide, an oligosaccharide, a polysaccharide or a mixture thereof.

In an advantageous embodiment, said cryoprotectant is chosen among sucrose, trehalose, glucose, inulin or a mixture thereof.

In one embodiment, said osmoprotectant is ectoine.

In one embodiment, said antioxidant is chosen among GSH, EGCG, ascorbic acid or a mixture thereof.

In one embodiment, said other additive is chosen among polymers, copolymers, amino-acids, in particular L-proline, peptides, proteins or a mixture thereof.

In an advantageous embodiment, the present invention relates to a lyophilized composition as defined above, wherein said culture medium is chosen among DMEM, RPMI or PBS, wherein said cryoprotectant is chosen among sucrose, trehalose, glucose, DMSO, inulin or a mixture thereof, wherein said osmoprotectant is ectoine, wherein said antioxidant is chosen among GSH, EGCG, ascorbic acid or a mixture thereof and wherein said other additive is chosen among polymers, copolymers, amino-acids, in particular L-proline, peptides, proteins or a mixture thereof.

In an advantageous embodiment, the lyophilized composition as defined above comprises:

DMEM, RPMI or PBS components,

0 µmole to about 300 µmole sucrose, in particular 0 µmole, 100 µmole or 150 µmole, 0 µmole to about 1000 µmole trehalose, in particular 0 µmole, 100 µmole, 200 µmole or 880 µmole, 0 µmole to about 400 µmole (fructose equivalent) inulin, in particular 0 µmole, 155 µmole or 309 µmole, 0 µmole to about 400 µmole ascorbic acid, in particular 0 µmole or 284 µmole, 0 µmole to about 10 µmole EGCG, in particular 0 µmole or 2 µmole, 0 µmole to about 200 µmole GSH, in particular 0 µmole or 100 µmole, 0 µmole to about 150 µmole proline, in particular 0 µmole or 87 µmole, 0 µmole to about 150 µmole ectoine, in particular 0 µmole or 63 µmole, said micromolar values being given for 1 mL of the suspension to be lyophilized, provided that the quantity of at least one of the components among sucrose, trehalose, inulin, ascorbic acid, EGCG, GSH, proline or ectoine is different from 0 µmole.

In another advantageous embodiment, the lyophilized composition as defined above comprises:

DMEM, RPMI or PBS components,

0 µmole to about 300 µmole sucrose, in particular 0 µmole, 100 µmole or 150 µmole, 0 µmole to about 1000 µmole trehalose, in particular 0 µmole, 100 µmole, 200 µmole or 880 µmole, 0 µmole to about 400 µmole (fructose equivalent) inulin, in particular 0 µmole, 155 µmole or 309 µmole, 0 µmole to about 400 µmole ascorbic acid, in particular 0 µmole or 284 µmole, 0 µmole to about 10 µmole EGCG, in particular 0 µmole or 2 µmole, 0 µmole to about 200 µmole GSH, in particular 0 µmole or 100 µmole, 0 µmole to about 150 µmole proline, in particular 0 µmole or 87 µmole, 0 µmole to about 150 µmole ectoine, in particular 0 µmole or 70 µmole, said micromolar values being given for 1 mL of the suspension to be lyophilized, provided that the quantity of at least one of the components among sucrose, trehalose, inulin, ascorbic acid, EGCG, GSH, proline or ectoine is different from 0 µmole.

In an advantageous embodiment, the present invention relates to a lyophilized composition as defined above, wherein said freeze-dried protozoa are virulent protozoa, attenuated protozoa or avirulent protozoa.

In one embodiment, the present invention relates to a lyophilized composition as defined above, wherein said freeze-dried protozoa are virulent protozoa, said lyophilized composition being capable of reconstitution to produce a rehydrated lyophilized composition of virulent protozoa.

In another embodiment, the present invention relates to a lyophilized composition as defined above, wherein said freeze-dried protozoa are avirulent or attenuated protozoa, said lyophilized composition being capable of reconstitution to produce a vaccine composition or an immunostimulant.

In one embodiment, said freeze-dried protozoa belong to the subgroup of Sporozoan or of *Flagellates*.

In one embodiment, said freeze-dried protozoa belong to the phylum of Apicomplexa.

In another embodiment, said freeze-dried protozoa belong to the phylum of Apicomplexa or of Euglenozoa.

In one embodiment, said freeze-dried protozoa belong to the family of Sarcocystidae.

In another embodiment, said freeze-dried protozoa belong to the family of Sarcocystidae or of Plasmodiidae or of Trypanosomatidae.

In one embodiment, said freeze-dried protozoa are live attenuated strains of *Toxoplasma* spp. or of *Neospora* spp.

In one embodiment, said freeze-dried protozoa are recombinant live attenuated strains of *Toxoplasma* spp., of *Neospora* spp., of *Sarcocystis* spp. or a combination of said strains.

In one embodiment, said freeze-dried protozoa are recombinant live attenuated strains of *Toxoplasma gondii*, of *Neospora caninum*, of *Neospora hughesi*, of *Sarcocystis neurona* or a combination of said strains.

In one embodiment, said freeze-dried protozoa are recombinant and/or live attenuated strains of *Leishmania* spp.

In one embodiment, said freeze-dried protozoa are recombinant and/or live attenuated strains of *Leishmania donovani*, of *Leishmania infantum* or a combination of said strains.

In one embodiment, said freeze-dried protozoa are recombinant and/or live attenuated strains of *Plasmodium* spp.

In one embodiment, said freeze-dried protozoa are recombinant and/or live attenuated strains of *Plasmodium falciparum*.

In one embodiment, said freeze-dried protozoa are live attenuated strains of *Toxoplasma* spp. or of *Neospora* spp. or of *Sarcocystis* spp. or of *Plasmodium* spp. or of *Leishmania* spp.

In one embodiment, said freeze-dried protozoa are recombinant live attenuated strains of *Toxoplasma* spp., of *Neospora* spp., of *Sarcocystis* spp., of *Plasmodium* spp., of *Leishmania* spp. or a combination of said strains.

In one embodiment, said freeze-dried protozoa are recombinant live attenuated strains of *Toxoplasma gondii*, of *Neospora caninum*, of *Neospora hughesi*, of *Sarcocystis neurona*, of *Plasmodium falciparum*, of *Plasmodium vivax*, of *Leishmania donovavi*, of *Leishmania infantum* or a combination of said strains.

In another aspect, the invention relates to a process for obtaining a lyophilized composition containing freeze-dried protozoa of intracellular nature, devoid of protozoal host cells, containing a moisture content of less than 12% by weight and being capable of reconstitution to restore said protozoa to viable and infectious states, said viable protozoa accounting for more than 1% of the freeze-dried protozoa, comprising a step of freeze-drying a suspension of protozoa of intracellular nature, devoid of protozoal host cells, in an aqueous formulation solution.

In an advantageous embodiment, the invention relates to a process as defined above, for obtaining a lyophilized composition being capable of reconstitution to restore said protozoa to viable and infectious states after a storage for a period of time longer than two weeks at a temperature from −25° C. to +25° C., in particular at a temperature from −25° C. to 2° C., at a temperature from 2 to 8° C., more particularly at a temperature from 2 to 6° C., or at a temperature from 8 to 25° C.

In one embodiment, the invention related to a process for obtaining a lyophilized composition containing freeze-dried protozoa of intracellular nature, devoid of protozoal host cells, containing a moisture content of less than 12% by weight and being capable of reconstitution to restore said protozoa to viable and infectious states, said viable protozoa accounting for more than 1% of the freeze-dried protozoa, in particular after a storage for a period of time longer than two weeks at a temperature from −25° C. to +25° C., in particular at a temperature from −25° C. to 2° C., at a temperature from 2 to 8° C., more particularly at a temperature from 2 to 6° C., or at a temperature from 8 to 25° C., comprising a step of freeze-drying a suspension of protozoa of intracellular nature, devoid of protozoal host cells, in an aqueous formulation solution, said step of freeze-drying said suspension comprising:

a step of primary drying of a frozen suspension to obtain a primary dried composition, in particular said step of primary drying is carried out at about −55° C., for about 20 h and in particular said step of primary drying is carried out at a pressure comprised from about 30 to about 80 Pa, for 0 to 7 h, and then at a pressure below 2 Pa for the rest of the time, and a step of secondary drying of the primary dried composition to obtain a lyophilized composition with a moisture content of less than 12% by weight, in particular said step of secondary drying is carried out at a pressure below 2 Pa and at a temperature increasing from −55° C. to +5° C. at a rate comprised from about 0.01° C./min to about 0.2° C./min, in particular at a rate of about 0.0625° C./min and in particular said secondary drying comprises a temperature plateau of 1 h at every increase of 15° C., said temperature being maintained at +5° C. for 4 h when reaching said temperature.

In one embodiment, the invention relates to a process as defined above, wherein the step of freeze-drying said suspension comprises a step of freezing the suspension to obtain a frozen suspension.

In an advantageous embodiment, the step of freezing is carried out for 4 to 23 h, at atmospheric pressure, by lowering the initial temperature of the suspension of protozoa to a temperature comprised from about −40° C. to about −80° C., in particular about −75° C., said initial temperature of the suspension of protozoa being comprised from about 15° C. to about 25° C., in particular about 20° C., and said lowering of the temperature being carried out at a rate comprised from about −0.1° C./min to about −10° C./min, in particular at a rate of about −1° C./min.

In this embodiment, the step of freezing starts after a period of time comprised from 0 to 2 h after the formation of the suspension.

In one embodiment, the invention relates to a process as defined above, comprising a step of primary drying of said frozen suspension to obtain a primary dried composition.

In an advantageous embodiment, said step of primary drying is carried out at about −55° C., for about 20 h.

In an advantageous embodiment, said step of primary drying is carried out at a pressure comprised from about 30 to about 80 Pa, for 0 to 7 h, and then at a pressure below 2 Pa for the rest of the time.

In one embodiment, the invention relates to a process as defined above, comprising a step of secondary drying of the primary dried composition to obtain a lyophilized composition with a moisture content of less than 12% by weight.

In an advantageous embodiment, said step of secondary drying is carried out at a pressure below 2 Pa and at a temperature increasing from −55° C. to +5° C. at a rate comprised from about 0.01° C./min to about 0.2° C./min, in particular at a rate of about 0.0625° C./min.

In an advantageous embodiment said secondary drying comprises a temperature plateau of 1 h at every increase of 15° C., said temperature being maintained at +5° C. for 4 h when reaching said temperature.

In an advantageous embodiment, the invention relates to a process as defined above, wherein the step of freeze-drying said suspension comprises a step of freezing the suspension to obtain a frozen suspension, in particular said step of freezing is carried out for 4 to 23 h, at atmospheric pressure, by lowering the initial temperature of the suspension of protozoa to a temperature comprised from about −40° C. to about −80° C., in particular about −75° C., said initial temperature of the suspension of protozoa being comprised from about 15° C. to about 25° C., in particular about 20° C., and said lowering of the temperature being carried out at a rate comprised from about −0.1° C./min to about −10° C./min, in particular at a rate of about −1° C./min, a step of primary drying of said frozen suspension to obtain a primary dried composition, in particular said step of primary drying is carried out at about −55° C., for about 20 h and in particular said step of primary drying is carried out at a pressure comprised from about 30 to about 80 Pa, for 0 to 7 h, and then at a pressure below 2 Pa for the rest of the time, and a step of secondary drying of the primary dried composition to obtain a lyophilized composition with a moisture content of less than 12% by weight, in particular said step of secondary drying is carried out at a pressure below 2 Pa and at a temperature increasing from −55° C. to +5° C. at a rate comprised from about 0.01° C./min to about 0.2° C./min, in particular at a rate of about 0.0625° C./min and in particular said secondary drying comprises a temperature plateau of 1 h at every increase of 15° C., said temperature being maintained at +5° C. for 4 h when reaching said temperature.

In one embodiment, the invention relates to a process as defined above, comprising an initial step of suspending protozoa of intracellular nature and devoid of protozoal host cells in an aqueous formulation solution comprising a culture medium of said protozoa and at least one cryoprotectant to obtain a suspension of protozoa in an aqueous formulation solution.

In one embodiment, said aqueous formulation solution further comprises at least one osmoprotectant and/or at least one antioxidant and/or at least one other additive.

In one embodiment said aqueous formulation solution comprises a culture medium of said protozoa, at least one cryoprotectant, at least one osmoprotectant, at least one antioxidant and/or at least one other additive.

In an advantageous embodiment, the culture medium in said aqueous formulation solution is chosen among DMEM, RPMI or PBS.

In an advantageous embodiment, the cryoprotectant in said formulation solution is chosen among DMSO, a monosaccharide, a disaccharide, an oligosaccharide, a polysaccharide or a mixture thereof.

In an advantageous embodiment, the cryoprotectant in said formulation solution is chosen among sucrose, trehalose, glucose, inulin or a mixture thereof.

In an advantageous embodiment, the osmoprotectant in said formulation solution is ectoine.

In an advantageous embodiment, the antioxidant in said formulation solution is chosen among GSH, EGCG, ascorbic acid or a mixture thereof.

In an advantageous embodiment, the other additive in said formulation solution is chosen among polymers, copolymers, amino-acids, in particular L-proline, peptides, proteins or a mixture thereof. In an advantageous embodiment, the culture medium in said aqueous formulation solution is chosen among DMEM, RPMI or PBS, wherein the cryoprotectant in said formulation solution is chosen among sucrose, trehalose, glucose, DMSO, inulin or a mixture thereof, wherein the osmoprotectant in said formulation solution is ectoine, wherein the antioxidant in said formulation solution are is chosen among GSH, EGCG, ascorbic acid or a mixture thereof and wherein the other additive in said formulation solution is chosen among polymers, copolymers, amino-acids, in particular L-proline, peptides, proteins or a mixture thereof.

In an advantageous embodiment, the present invention relates to a process as defined above, wherein said aqueous formulation solution A comprises or consists in:

DMEM, RPMI or PBS, 0 mM to about 3000 mM DMSO, in particular 0 mM or 1405 mM, 0 mM to about 300 mM sucrose, in particular 0 mM, 100 mM or 150 mM, 0 mM to about 1000 mM trehalose, in particular 0 mM, 100 mM, 200 mM or 880 mM, 0 mM to about 400 mM (fructose equivalent) inulin, in particular 0 mM, 155 mM or 309 mM, 0 mM to about 400 mM ascorbic acid, in particular 0 mM or 284 mM, 0 mM to about 10 mM EGCG, in particular 0 mM or 2 mM, 0 mM to about 200 mM GSH, in particular 0 mM or 100 mM, 0 mM to about 150 mM proline, in particular 0 mM or 87 mM, 0 mM to about 150 mM ectoine, in particular 0 mM or 63 mM, provided that the concentration of at least one of the components among DMSO, sucrose, trehalose, inulin, ascorbic acid, EGCG, GSH, proline or ectoine is different from 0 mM.

In another advantageous embodiment, the present invention relates to a process as defined above, wherein said aqueous formulation solution B comprises or consists in:

DMEM, RPMI or PBS, 0 mM to about 3000 mM DMSO, in particular 0 mM or 1280 mM, 0 mM to about 300 mM sucrose, in particular 0 mM, 100 mM or 150 mM, 0 mM to about 1000 mM trehalose, in particular 0 mM, 100 mM, 200 mM or 880 mM, 0 mM to about 400 mM (fructose equivalent) inulin, in particular 0 mM, 155 mM or 309 mM, 0 mM to about 400 mM ascorbic acid, in particular 0 mM or 284 mM, 0 mM to about 10 mM EGCG, in particular 0 mM or 2 mM, 0 mM to about 200 mM GSH, in particular 0 mM or 100 mM, 0 mM to about 150 mM proline, in particular 0 mM or 87 mM, 0 mM to about 150 mM ectoine, in particular 0 mM or 70 mM,
provided that the concentration of at least one of the components among DMSO, sucrose, trehalose, inulin, ascorbic acid, EGCG, GSH, proline or ectoine is different from 0 mM.

In one embodiment, said aqueous formulation solution comprises or consists in:
DMEM
20 mM to about 300 mM trehalose
20 mM to about 300 mM sucrose
20 mM to about 400 mM (fructose equivalent) autoclaved inulin
20 mM to about 200 mM GSH
20 mM to about 150 mM ectoine
20 mM to about 150 mM proline
and is adjusted at pH 7.4 with sodium hydroxide.
By "consists in" it is understood that in the above formulation, the following elements: DMSO, ascorbic acid and EGCG are all absent.
By "comprises", it is understood that
either at least one of the following elements: DMSO, ascorbic acid and EGCG is absent, the other elements being at the concentrations defined above in formulation A or in formulation B and different from 0 mM,
or all the elements DMSO, ascorbic acid and EGCG are present at the concentrations defined above in formulation A or in formulation B and are different from 0 mM.

In another embodiment, said aqueous formulation solution comprises or consists in:
DMEM
20 mM to about 300 mM trehalose
20 mM to about 400 mM ascorbic acid
and is adjusted at pH 7.4 with sodium hydroxide.
By "consists in" it is understood that in the above formulation, the following elements: DMSO, sucrose, inulin, EGCG, GSH, proline and ectoine are all absent.
By "comprises", it is understood that
either at least one of the following elements: DMSO, sucrose, inulin, EGCG, GSH, proline and ectoine is absent, the other elements being at the concentrations defined above in formulation A or in formulation B and different from 0 mM,
or all the elements DMSO, sucrose, inulin, EGCG, GSH, proline and ectoine are present at the concentrations defined above in formulation A or in formulation B and are different from 0 mM.

In another embodiment, said aqueous formulation solution comprises or consists in:
DMEM
20 mM to about 300 mM trehalose
20 mM to about 300 mM sucrose
20 mM to about 400 mM (fructose equivalent) inulin.
By "consists in" it is understood that in the above formulation, the following elements: DMSO, ascorbic acid, EGCG, GSH, proline and ectoine are all absent.
By "comprises", it is understood that
either at least one of the following elements: DMSO, ascorbic acid, EGCG, GSH, proline and ectoine is absent, the other elements being at the concentrations defined above in formulation A or in formulation B and different from 0 mM,
or all the elements DMSO, ascorbic acid, EGCG, GSH, proline and ectoine are present at the concentrations defined above in formulation A or in formulation B and are different from 0 mM.

In another embodiment, said aqueous formulation solution comprises or consists in:
DMEM
20 mM to about 300 mM trehalose
20 mM to about 300 mM sucrose
20 mM to about 200 mM GSH
20 mM to about 150 mM ectoine
20 mM to about 150 mM proline
and is adjusted at pH 7.4 with sodium hydroxide.
By "consists in" it is understood that in the above formulation, the following elements: DMSO, inulin, ascorbic acid and EGCG are all absent.
By "comprises", it is understood that
either at least one of the following elements: DMSO, inulin, ascorbic acid and EGCG is absent, the other elements being at the concentrations defined above in formulation A or in formulation B and different from 0 mM,
or all the elements DMSO, inulin, ascorbic acid and EGCG are present at the concentrations defined above in formulation A or in formulation B and are different from 0 mM.

In another embodiment, said aqueous formulation solution comprises or consists in:
DMEM
200 mM to about 3000 mM DMSO.
By "consists in" it is understood that in the above formulation, the following elements: trehalose, sucrose, inulin, ascorbic acid, EGCG, GSH, proline and ectoine are all absent.
By "comprises", it is understood that
either at least one of the following elements: trehalose, sucrose, inulin, ascorbic acid, EGCG, GSH, proline and ectoine is absent, the other elements being at the concentrations defined above in formulation A or in formulation B and different from 0 mM,
or all the elements trehalose, sucrose, inulin, ascorbic acid, EGCG, GSH, proline and ectoine are present at the concentrations defined above in formulation A or in formulation B and are different from 0 mM.

In another embodiment, said aqueous formulation solution comprises or consists in:
DMEM
20 mM to about 300 mM trehalose
0.1 mM to about 10 mM EGCG.
By "consists in" it is understood that in the above formulation, the following elements: DMSO, sucrose, inulin, ascorbic acid, GSH, proline and ectoine are all absent.
By "comprises", it is understood that
either at least one of the following elements: DMSO, sucrose, inulin, ascorbic acid, GSH, proline and ectoine is absent, the other elements being at the concentrations defined above in formulation A or in formulation B and different from 0 mM,
or all the elements DMSO, sucrose, inulin, ascorbic acid, GSH, proline and ectoine are present, at the concentrations defined above in formulation A or in formulation B and are different from 0 mM.

In another embodiment, said aqueous formulation solution comprises or consists in:
PBS
20 mM to about 300 mM trehalose
20 mM to about 300 mM sucrose
20 mM to about 400 mM (fructose equivalent) autoclaved inulin
20 mM to about 200 mM GSH
20 mM to about 150 mM ectoine 20 mM to about 150 mM proline
and is adjusted at pH 7.4 with sodium hydroxide.

By "consists in" it is understood that in the above formulation, the following elements: DMSO, ascorbic acid and EGCG are all absent.

By "comprises", it is understood that
either at least one of the following elements: DMSO, ascorbic acid and EGCG is absent, the other elements being at the concentrations defined above in formulation A or in formulation B and different from 0 mM,
or all the elements DMSO, ascorbic acid and EGCG are present at the concentrations defined above in formulation A or in formulation B and are different from 0 mM.

In one embodiment, said aqueous formulation solution comprises or consists in:
DMEM
0.1 M trehalose
0.1 M sucrose
2.5% autoclaved inulin
0.1 M GSH
1% ectoine
1% proline
and is adjusted at pH 7.4 with sodium hydroxide.

By "consists in" it is understood that in the above formulation, the following elements: DMSO, ascorbic acid and EGCG are all absent.

By "comprises", it is understood that
either at least one of the following elements: DMSO, ascorbic acid and EGCG is absent, the other elements being at the concentrations defined above in formulation A or in formulation B and different from 0 mM,
or all the elements DMSO, ascorbic acid and EGCG are present at the concentrations defined above in formulation A or in formulation B and are different from 0 mM.

In another embodiment, said aqueous formulation solution comprises or consists in:
DMEM
0.1 M trehalose
5% ascorbic acid
and is adjusted at pH 7.4 with sodium hydroxide.

By "consists in" it is understood that in the above formulation, the following elements: DMSO, sucrose, inulin, EGCG, GSH, proline and ectoine are all absent.

By "comprises", it is understood that
either at least one of the following elements: DMSO, sucrose, inulin, EGCG, GSH, proline and ectoine is absent, the other elements being at the concentrations defined above in formulation A or in formulation B and different from 0 mM,
or all the elements DMSO, sucrose, inulin, EGCG, GSH, proline and ectoine are present at the concentrations defined above in formulation A or in formulation B and are different from 0 mM.

In another embodiment, said aqueous formulation solution comprises or consists in:
DMEM
0.1 M trehalose
0.1 M sucrose
5% inulin.

By "consists in" it is understood that in the above formulation, the following elements: DMSO, ascorbic acid, EGCG, GSH, proline and ectoine are all absent.

By "comprises", it is understood that
either at least one of the following elements: DMSO, ascorbic acid, EGCG, GSH, proline and ectoine is absent, the other elements being at the concentrations defined above in formulation A or in formulation B and different from 0 mM,
or all the elements DMSO, ascorbic acid, EGCG, GSH, proline and ectoine are present at the concentrations defined above in formulation A or in formulation B and are different from 0 mM.

In another embodiment, said aqueous formulation solution comprises or consists in:
DMEM
0.2 M trehalose
0.15 M sucrose
0.1 M GSH
1% ectoine
1% proline
and is adjusted at pH 7.4 with sodium hydroxide.

By "consists in" it is understood that in the above formulation, the following elements: DMSO, inulin, ascorbic acid and EGCG are all absent.

By "comprises", it is understood that
either at least one of the following elements: DMSO, inulin, ascorbic acid and EGCG is absent, the other elements being at the concentrations defined above in formulation A or in formulation B and different from 0 mM,
or all the elements DMSO, inulin, ascorbic acid and EGCG are present at the concentrations defined above in formulation A or in formulation B and are different from 0 mM.

In another embodiment, said aqueous formulation solution comprises or consists in:
DMEM
10% DMSO.

By "consists in" it is understood that in the above formulation, the following elements: trehalose, sucrose, inulin, ascorbic acid, EGCG, GSH, proline and ectoine are all absent.

By "comprises", it is understood that
either at least one of the following elements: trehalose, sucrose, inulin, ascorbic acid, EGCG, GSH, proline and ectoine is absent, the other elements being at the concentrations defined above in formulation A or in formulation B and different from 0 mM,
or all the elements trehalose, sucrose, inulin, ascorbic acid, EGCG, GSH, proline and ectoine are present at the concentrations defined above in formulation A or in formulation B and are different from 0 mM.

In another embodiment, said aqueous formulation solution comprises or consists in:
DMEM
0.1 M trehalose
1 mg/mL EGCG.

By "consists in" it is understood that in the above formulation, the following elements: DMSO, sucrose, inulin, ascorbic acid, GSH, proline and ectoine are all absent.

By "comprises", it is understood that
either at least one of the following elements: DMSO, sucrose, inulin, ascorbic acid, GSH, proline and ectoine is absent, the other elements being at the concentrations defined above in formulation A or in formulation B and different from 0 mM,
or all the elements DMSO, sucrose, inulin, ascorbic acid, GSH, proline and ectoine are present at the concentrations defined above in formulation A or in formulation B and are different from 0 mM.

In another embodiment, said aqueous formulation solution comprises or consists in:

PBS
0.1 M trehalose
0.1 M sucrose
2.5% autoclaved inulin
0.1 M GSH
1% ectoine
1% proline
and is adjusted at pH 7.4 with sodium hydroxide.

By "consists in" it is understood that in the above formulation, the following elements: DMSO, ascorbic acid and EGCG are all absent.

By "comprises", it is understood that
either at least one of the following elements: DMSO, ascorbic acid and EGCG is absent, the other elements being at the concentrations defined above in formulation A or in formulation B and different from 0 mM,
or all the elements DMSO, ascorbic acid and EGCG are present at the concentrations defined above in formulation A or in formulation B and are different from 0 mM.

In an advantageous embodiment, the present invention relates to a process as defined above, comprising the steps of:
suspending said protozoa in a aqueous formulation solution comprising
DMEM, RPMI or PBS
0 mM to about 3000 mM DMSO, in particular 0 mM or 1405 mM,
0 mM to about 300 mM sucrose, in particular 0 mM, 100 mM or 150 mM,
0 mM to about 1000 mM trehalose, in particular 0 mM, 100 mM, 200 mM or 880 mM,
0 mM to about 400 mM (fructose equivalent) inulin, in particular 0 mM, 155 mM or 309 mM,
0 mM to about 400 mM ascorbic acid, in particular 0 mM or 284 mM,
0 mM to about 10 mM EGCG, in particular 0 mM or 2 mM,
0 mM to about 200 mM GSH, in particular 0 mM or 100 mM,
0 mM to about 150 mM proline, in particular 0 mM or 87 mM,
0 mM to about 150 mM ectoine, in particular 0 mM or 63 mM,
provided that the concentration of at least one of the components among DMSO, sucrose, trehalose, inulin, ascorbic acid, EGCG, GSH, proline or ectoine is different from 0 mM, to obtain a suspension of protozoa in said aqueous formulation solution.

freezing said suspension for 4 to 23 h, at atmospheric pressure, by lowering the initial temperature of the suspension of protozoa to a temperature comprised from about −40° C. to about −80° C., in particular about −75° C., said initial temperature of the suspension of protozoa being comprised from about 15° C. to about 25° C., in particular about 20° C., and said lowering of the temperature being carried out at a rate comprised from about −0.1° C./min to about −10° C./min, in particular at a rate of about −1° C./min, to obtain a frozen suspension.

subjecting said frozen suspension to a primary drying at about −55° C. for about 20 h and at a pressure comprised from about 30 to about 80 Pa for 0 to 7 h, then at a pressure below 2 Pa for the rest of the time, to obtain a primary dried composition.

subjecting said primary dried composition to a secondary drying at a pressure below 2 Pa and at a temperature increasing from −55° C. to +5° C. at a rate comprised from about 0.01° C./min to about 0.2° C./min, in particular at a rate of about 0.0625° C./min, said secondary drying comprising a temperature plateau of 1 h at every increase of 15° C. and said temperature being maintained at +5° C. for 4 h when reaching said temperature, to obtain said lyophilized composition.

In another advantageous embodiment, the present invention relates to a process as defined above, comprising the steps of:
suspending said protozoa in a aqueous formulation solution comprising
DMEM, RPMI or PBS
0 mM to about 3000 mM DMSO, in particular 0 mM or 1280 mM,
0 mM to about 300 mM sucrose, in particular 0 mM, 100 mM or 150 mM,
0 mM to about 1000 mM trehalose, in particular 0 mM, 100 mM, 200 mM or 880 mM,
0 mM to about 400 mM (fructose equivalent) inulin, in particular 0 mM, 155 mM or 309 mM,
0 mM to about 400 mM ascorbic acid, in particular 0 mM or 284 mM,
0 mM to about 10 mM EGCG, in particular 0 mM or 2 mM,
0 mM to about 200 mM GSH, in particular 0 mM or 100 mM,
0 mM to about 150 mM proline, in particular 0 mM or 87 mM,
0 mM to about 150 mM ectoine, in particular 0 mM or 70 mM,
provided that the concentration of at least one of the components among DMSO, sucrose, trehalose, inulin, ascorbic acid, EGCG, GSH, proline or ectoine is different from 0 mM, to obtain a suspension of protozoa in said aqueous formulation solution.

freezing said suspension for 4 to 23 h, at atmospheric pressure, by lowering the initial temperature of the suspension of protozoa to a temperature comprised from about −40° C. to about −80° C., in particular about −75° C., said initial temperature of the suspension of protozoa being comprised from about 15° C. to about 25° C., in particular about 20° C., and said lowering of the temperature being carried out at a rate comprised from about −0.1° C./min to about −10° C./min, in particular at a rate of about −1° C./min, to obtain a frozen suspension.

subjecting said frozen suspension to a primary drying at about −55° C. for about 20 h and at a pressure comprised from about 30 to about 80 Pa for 0 to 7 h, then at a pressure below 2 Pa for the rest of the time, to obtain a primary dried composition.

subjecting said primary dried composition to a secondary drying at a pressure below 2 Pa and at a temperature increasing from −55° C. to +5° C. at a rate comprised from about 0.01° C./min to about 0.2° C./min, in particular at a rate of about 0.0625° C./min, said secondary drying comprising a temperature plateau of 1 h at every increase of 15° C. and said temperature being maintained at +5° C. for 4 h when reaching said temperature, to obtain said lyophilized composition.

In another aspect, the invention relates to a lyophilized composition such as obtained by the process as defined above.

In another aspect, the invention relates to a rehydrated lyophilized composition comprising a lyophilized composition as defined above in a rehydration medium, wherein said lyophilized composition contains freeze-dried protozoa of intracellular nature, is devoid of protozoal host cells and contains a moisture content of less than 12% by weight, said rehydrated lyophilized composition being such that the protozoa contained in it are viable and infectious and said viable protozoa accounting for more than 1% of the freeze-dried protozoa.

In an advantageous embodiment, the invention relates to a rehydrated lyophilized composition as defined above, wherein the protozoa are viable and infectious after a storage, before reconstitution, of said lyophilized composition for a period of time longer than two weeks at a temperature from −25 to 25° C., in particular at a temperature from −25° C. to 2° C., at a temperature from 2 to 8° C., more particularly at a temperature from 2 to 6° C., or at a temperature from 8 to 25° C.

In one advantageous embodiment, the present invention relates to a rehydrated lyophilized composition as defined above, wherein said rehydration medium is a culture medium of said protozoa.

In one advantageous embodiment, said rehydration medium is the same culture medium as the cultured medium in the aqueous formulation composition wherein the protozoa are suspended before freeze-drying.

In an advantageous embodiment, said rehydration medium is DMEM.

In an advantageous embodiment, the present invention relates to a rehydrated lyophilized composition as defined above, comprising DMEM, RPMI or PB S 0 mM to about 300 mM sucrose, in particular 0 mM, 100 mM or 150 mM, 0 mM to about 1000 mM trehalose, in particular 0 mM, 100 mM, 200 mM or 880 mM, 0 mM to about 400 mM (fructose equivalent) inulin, in particular 0 mM, 155 mM or 309 mM, 0 mM to about 400 mM ascorbic acid, in particular 0 mM or 284 mM, 0 mM to about 10 mM EGCG, in particular 0 mM or 2 mM, 0 mM to about 200 mM GSH, in particular 0 mM or 100 mM, 0 mM to about 150 mM proline, in particular 0 mM or 87 mM, 0 mM to about 150 mM ectoine, in particular 0 mM or 63 mM, provided that the concentration of at least one of the components among sucrose, trehalose, inulin, ascorbic acid, EGCG, GSH, proline or ectoine is different from 0 mM.

In another advantageous embodiment, the present invention relates to a rehydrated lyophilized composition as defined above, comprising DMEM, RPMI or PB S 0 mM to about 300 mM sucrose, in particular 0 mM, 100 mM or 150 mM, 0 mM to about 1000 mM trehalose, in particular 0 mM, 100 mM, 200 mM or 880 mM, 0 mM to about 400 mM (fructose equivalent) inulin, in particular 0 mM, 155 mM or 309 mM, 0 mM to about 400 mM ascorbic acid, in particular 0 mM or 284 mM, 0 mM to about 10 mM EGCG, in particular 0 mM or 2 mM, 0 mM to about 200 mM GSH, in particular 0 mM or 100 mM, 0 mM to about 150 mM proline, in particular 0 mM or 87 mM, 0 mM to about 150 mM ectoine, in particular 0 mM or 70 mM, provided that the concentration of at least one of the components among sucrose, trehalose, inulin, ascorbic acid, EGCG, GSH, proline or ectoine is different from 0 mM.

In another aspect, the present invention relates to a therapeutic or vaccinal composition comprising the rehydrated lyophilized composition as defined above.

In another aspect, the present invention relates to a process for reconstituting a lyophilized composition as defined above, said lyophilized composition containing freeze-dried protozoa of intracellular nature, being devoid of protozoal host cells and containing a moisture content of less than 12% by weight, comprising a step of adding a rehydration medium to said lyophilized composition to obtain a rehydrated lyophilized composition wherein said protozoa are viable and infectious, said viable protozoa accounting for more than 1% of the freeze-dried protozoa.

In an advantageous embodiment, the present invention relates to a process as defined above, to obtain a rehydrated lyophilized composition wherein said protozoa are viable and infectious after a storage, before reconstitution, of said lyophilized composition for a period of time longer than two weeks at a temperature from −25 to 25° C., in particular at a temperature from −25° C. to 2° C., at a temperature from 2 to 8° C., more particularly at a temperature from 2 to 6° C., or at a temperature from 8 to 25° C.

In one embodiment, the present invention relates to a process as defined above, wherein the rehydration medium is a culture medium of said protozoa.

In an advantageous embodiment, the rehydration medium is the same culture medium as the culture medium in the aqueous formulation solution wherein said protozoa are suspended before freeze-drying.

In an advantageous embodiment, the rehydration medium is DMEM.

In an advantageous embodiment, the present invention relates to a process as defined above, wherein said step of adding the rehydration medium is carried out at a rate comprised from about 25 µL per second to about 1000 µL per second, in particular at a rate of about 250 µL per second.

In another aspect, the present invention relates to a suspension of protozoa of intracellular nature and devoid of protozoal host cells in an aqueous formulation solution, said aqueous formulation solution comprising:

DMEM, RPMI or PB S 0 mM to about 3000 mM DMSO, in particular 0 mM or 1405 mM, 0 mM to about 300 mM sucrose, in particular 0 mM, 100 mM or 150 mM, 0 mM to about 1000 mM trehalose, in particular 0 mM, 100 mM, 200 mM or 880 mM, 0 mM to about 400 mM (fructose equivalent) inulin, in particular 0 mM, 155 mM or 309 mM, 0 mM to about 400 mM ascorbic acid, in particular 0 mM or 284 mM, 0 mM to about 10 mM EGCG, in particular 0 mM or 2 mM, 0 mM to about 200 mM GSH, in particular 0 mM or 100 mM, 0 mM to about 150 mM proline, in particular 0 mM or 87 mM, 0 mM to about 150 mM ectoine, in particular 0 mM or 63 mM, provided that the concentration of at least one of the components among DMSO, sucrose, trehalose, inulin, ascorbic acid, EGCG, GSH, proline or ectoine is different from 0 mM.

In another embodiment, the present invention relates to a suspension of protozoa of intracellular nature and devoid of protozoal host cells in an aqueous formulation solution, said aqueous formulation solution comprising:

DMEM, RPMI or PB S 0 mM to about 3000 mM DMSO, in particular 0 mM or 1280 mM, 0 mM to about 300 mM sucrose, in particular 0 mM, 100 mM or 150 mM, 0 mM to about 1000 mM trehalose, in particular 0 mM, 100 mM, 200 mM or 880 mM, 0 mM to about 400 mM (fructose equivalent) inulin, in particular 0 mM, 155 mM or 309 mM, 0 mM to about 400 mM ascorbic acid, in particular 0 mM or 284 mM, 0 mM to about 10 mM EGCG, in particular 0 mM or 2 mM, 0 mM to about 200 mM GSH, in particular 0 mM or 100 mM, 0 mM to about 150 mM proline, in particular 0 mM or 87 mM, 0 mM to about 150 mM ectoine, in particular 0 mM or 70 mM, provided that the concentration of at least one of the components among DMSO, sucrose, trehalose, inulin, ascorbic acid, EGCG, GSH, proline or ectoine is different from 0 mM.

BRIEF DESCRIPTION OF THE DRAWINGS

This application contains no drawings.

DETAILED DESCRIPTION OF THE INVENTION

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

A "subject" in the context of the present invention can be a vertebrate, such as a mammal, bird, reptile, amphibian or fish; more advantageously a human, a companion or domesticated animal; a food-producing or feed-producing animal; livestock, game, racing or sport animal such as, but not limited to, bovines, canines, felines, caprines, ovines, porcines, equines, and avians. Preferably, the vertebrate is a canine.

An "antigen" is a substance that is recognized by the immune system and induces an immune response. The antigen may comprise a whole organism, killed, attenuated or live; a subunit or portion of an organism; a recombinant vector containing an insert with immunogenic properties; a nucleic acid piece or fragment capable of inducing an immune response upon presentation to a host animal; a protein, a polypeptide, a peptide, a glycoprotein, an epitope, a hapten, a carbohydrate, a sugar, or any combination thereof. Alternatively, the antigen may comprise a toxin or antitoxin. A similar term used interchangeably in this context is "immunogen". A "pathogen" refers to a specific causative agent of disease, such as a bacterium, fungus, protozoan, parasite, or virus.

As used herein, the terms "immunogenic composition" and "immunological composition" and "immunogenic or immunological composition" cover any composition that elicits an immune response against the antigen or immunogen of interest expressed from vectors; for instance, after administration into a subject, elicits an immune response against the targeted immunogen or antigen of interest. The terms "vaccinal composition" and "vaccine" and "vaccine composition" covers any composition that induces a protective immune response against the antigen of interest, or which efficaciously protects against the antigen; for instance, after administration or injection into the subject, elicits an protective immune response against the targeted antigen or immunogen or provides efficacious protection against the antigen or immunogen expressed from vectors.

As used herein, the term "multivalent" means an immunogenic composition or vaccine composition containing more than one antigen, whether from the same species, from different species, or an immunogenic composition or vaccine composition containing a combination of antigens from different genera.

An "active immunogenic component" in the context of the present invention includes live attenuated pathogens, such as live attenuated viruses, live attenuated bacteria, fungi, or parasites. Also encompassed by the invention are recombinant heterologous immunogens or antigens derived from or originating from one or more pathogens described herein, which can be contained and expressed in, inter alia, viral vectors, bacterial vectors, fungal vectors, and plasmid vectors. The invention also comprehends epitopes of heterologous immunogens or antigens derived from one or more pathogens, immunomodulators such as cytokines, therapeutic agents, toxins, antibodies, antigen-binding fragments of an antibody, adjuvants, or other species such as antisense RNAs, catalytic RNAs, small interfering RNAs, among others.

The term "veterinary composition" means any composition comprising a vector for veterinary use expressing a therapeutic protein as, for example, erythropoietin (EPO) or an immunomodulatory protein, such as, for example, interferon (IFN). Similarly, the term "pharmaceutical composition" means any composition comprising a vector for expressing a therapeutic protein.

The compositions and methods of the present invention can be appropriately applied in the stabilization of any biological substance/agent or combination biologic substance/agent plus pharmaceutical/veterinary agent. "Biologics" include, but are not limited to, immunomodulators such as cytokines, therapeutic agents, toxins, antibodies, antigen-binding fragments of an antibody, adjuvants, or other species such as antisense RNAs, catalytic RNAs, small interfering RNAs, among others. After reconstitution of the vitrified materials/substances, these compounds may be used for the prevention of diseases as prophylactic immunization or provide relief against symptoms of disease as therapeutic immunization.

The invention encompasses a method for freeze-drying protozoan parasites, including intracellular parasites, including parasites from the Apicomplexa phylum and the Sarcocystidae family, and including *T gondii*. Prior to freeze-drying, the protozoans may be combined with at least one stabilizer, for example sugars or antioxidant compounds.

In some embodiments, freeze-drying stabilizers can optionally comprise at least one non-reducing oligosaccharide and/or at least one bulking agent and/or at least one sugar alcohol. These stabilizers can preserve or assist in retention of the immunogenicity, infectivity, and viability of biological ingredients including, but not limited to, viruses, bacteria, fungi, parasites, proteins, polypeptides, among others. Stabilizers used in the inventive freeze-drying methods may have a good aspect, including for example, uniform shape and color, and are safe for administration into a subject.

In some embodiments, the protozoan parasites are combined into a suspension comprising various protectants, which are present in the suspension to preserve the parasites' viability, infectivity, and immunogenicity before, during and after freeze-drying.

"Non-reducing oligosaccharides" in the context of the invention are sugars comprising from two to ten saccharide units and are unable to reduce another compound during oxidation-reduction reactions. In the present invention, the non-reducing oligosaccharide can be a non-reducing disaccharide or non-reducing trisaccharide, advantageously comprising trehalose, sucrose, or raffinose. The inventive stabilizers can also comprise a mixture of at least two non-reducing oligosaccharides.

"Inulin" is a polysaccharide composed of fructose unit chains (linked by D-fructosyl fructose bonds) of various lengths with a glucose molecule at the end of each fructose chain. Oligosaccharides from inulin (FOS) have been shown to protect the membrane of bacteria during freeze-drying and enhance survival of freeze-dried bacteria. However, until the instant disclosure, it was not known whether *T gondii* eukaryotic parasites could be protected by inulin during freezing.

"Polyethylene glycols" (PEG) are linear low molecular weight polyether polymers made from monomers of ethylene glycol. It was reported that associated with a mixture of sugar (trehalose, lactose or mannitol), 1% PEG maintained the activity of freeze-dried enzymes (LDH and phosphofructokinase) (Prestrelski et al., 1993). PEG may be used in the practice of the disclosed freeze-drying methods.

"PVP-40" Polyvinylpyrrolidone is a water-soluble polymer made from the monomer N-vinylpyrrolidone. This polymer was used to protect protein from freeze-drying damage. A study reported that addition of PVP (40 kDa) and BSA to lactate dehydrogenase (LDH) resulted in stabilization of the enzyme during the freezing step by inhibiting dissociation of the enzyme during freezing. (Wang W. 2000. IJP. Lyophilization and development of a solid protein pharmaceuticals.)

"PLURONIC F68" is a nonionic surfactant used to lower the surface tension of cells. During the freezing process, the formation of a water-ice interface may cause protein denaturation, thus, the presence of a surfactant in the solution will reduce protein adsorption or aggregation to the water-ice interface. The combination of PLURONIC F68 with other excipients, such as sugars (trehalose) helped maintain the viability and infectivity of *F. tularensis* (intracellular bacteria) after foam drying (Ohtake S. et al., 2011).

"Gelatin" is a heterogeneous mixture of water-soluble peptides and proteins of high average molecular weights, derived from collagen. It is used in pharmaceutical industry as stabilizer and encapsulating agent. Gelatin (Vaccipro) was used by Ohtake S. et al. in a *Francisella tularensis* (intracellular bacteria) live vaccine formulation. (Satoshi O. et al., 2011. J Pharm Sci).

"Ectoine" is a cyclic tetrahydropyrimidine organic osmolyte discovered in halophilic bacteria. It has been characterized as an osmoprotectant and stabilizer for cells and biomolecules, and appears to preserve enzymes and whole cells against harmful conditions such as freezing, drying, or heating. A combination of ectoine and proline was used for optimization of cryopreservation protocol for human cells. (Freimark D. et al. 2011. Cryobiology).

An "acid antioxidant" compound is defined as a chemical compound that reacts with and neutralizes oxidants, free radicals (i.e., molecules with unpaired electrons), or chemicals that release free radicals. In the context of the present invention, the antioxidant compound may be in acid form. Acid antioxidants include, but are not limited to, ascorbic acid and/or acidic amino acids, such as aspartic acid and glutamic acid. Combinations of more than one acid antioxidant compound are suitable components of preparations freeze-dried according to the methods of the instant disclosure.

Bulking agents are also suitable components of compositions vitrified according to the instant disclosure. The bulking agents may be pharmaceutically or veterinarily acceptable polymers such as, but not limited to, dextran, maltodextrin, polyvinylpyrrolidone (PVP), crospovidone, and hydroxyethyl starch. Other non-limiting examples of starch derivatives include microcrystalline cellulose, methyl cellulose, carboxy methyl cellulose, hydroxypropylcellulose, hydroxyethyl methyl cellulose, and hydroxypropyl methyl cellulose. The bulking agents increase the T'g value of the biological compositions, allowing the use of higher temperatures during freezing. The "T'g value" is defined as the glass transition temperature, which corresponds to the temperature below which the frozen composition becomes vitreous. The bulking agent may assist in providing the good aspect observed in the vitrified masses of the instant disclosure, which masses have the general appearance of light, fluffy, cotton candy.

Some components, including stabilizers, of the biological preparations may not be readily soluble. However, it is well within the reach of the skilled person to substitute suitably analogous components (e.g. by selecting a more soluble component) and/or to adapt the amounts or quantities of the insoluble component present in the stabilizer for the purpose of obtaining a soluble stabilizer. The solubility of a component can be easily checked by a visual solubility test. A solubility test comprises the steps of adding all of the components of the stabilizer at a temperature of about 55° C., and mixing for about 30 minutes. After approximately 24 hours at room temperature and without any agitation, the stabilizer can be visually checked for appearance of precipitates. If the stabilizer is transparent or limpid, then all the components of the stabilizer are soluble.

In the context of the instant disclosure, the term "bulk vaccine composition" is intended to mean a composition which exits the final stage of the antigen production, purified or non-purified, monovalent, or after multivalent mixing. The term "a dry vaccine composition" is intended to mean a composition of which the residual water content is less than or equal to about 12%, for instance about 4%, or about 3%, and which is ready to be reconstituted with an aqueous solution in order to be used as a vaccine or directly in dry particulate form. The dry vaccine composition may also be ground and formulated with appropriate excipients, including binders, to produce orally suitable dosage units, for example, tablets and pills.

The active immunogenic component can be selected from protozoa and their antigens including, but are not limited to,

*Plasmodium* species, *Trypanosome* species, *Giardia* species, *Boophilus* species, *Babesia* species, *Entamoeba* species, *Eimeria* species, *Leishmania* species, *Schistosoma* species, *Brugia* species, *Fascida* species, *Dirofilaria* species, *Wuchereria* species, *Onchocerea* species, *Treponema* species, *Toxoplasma* species, *Cryptococcus* species, *Coccidia* species, *Histomoniasis* species, *Hexamitiasis* species, *Giardia* species, among others; nematodes. Methods for preparing immunogens derived from protozoa are known in the art.

In the present invention, the active immunogenic component can also comprise a therapeutic agent, a cytokine, a toxin, an immunomodulator, a protein, a peptide, an antibody, an antigen-binding fragment of an antibody, an adjuvant, or any other molecule encodable by DNA and desired for delivery to an animal or animal cell or tissue.

The cooling step (b) can occur at temperatures of less than about −40° C. (water freezing step). Drying the stabilized immunogenic suspensions or solution by sublimation of ice at low pressure (c) can occur at, for example, pressure lower than or equal to about 80 Pa.

For its use and administration into a subject, the freeze-dried immunogenic composition or vaccine composition can be reconstituted by rehydration with a solvent. The solvent is typically water, such as demineralized or distilled water, water-for-injection, but can also comprise physiological solutions or buffers, such as for example phosphate buffer solution (PBS), or adjuvants including, but not limited to, water-in-oil emulsions, *Corynebacterium parvum*, *Bacillus* Calmette Guerin, aluminum hydroxide, glucan, dextran sulfate, iron oxide, sodium alginate, Bacto-Adjuvant, certain synthetic polymers such as poly amino acids and copolymers of amino acids, saponin, "REGRESSIN" (Vetrepharm, Athens, Ga.), "AVRIDINE" (N, N-dioctadecyl-N',N'-bis(2-hydroxyethyl)-propanediamine), paraffin oil, muramyl dipeptide and the like. Other specific examples of adjuvants and adjuvant compositions are detailed herein.

Suitable adjuvants include fMLP (N-formyl-methionyl-leucyl-phenylalanine; U.S. Pat. No. 6,017,537) and/or acrylic acid or methacrylic acid polymer and/or a copolymer of maleic anhydride and of alkenyl derivative. The acrylic acid or methacrylic acid polymers can be cross-linked, e.g., with polyalkenyl ethers of sugars or of polyalcohols. These compounds are known under the term "carbomer" (*Pharmeuropa*, Vol. 8, No. 2, June 1996). A person skilled in the art may refer to U.S. Pat. No. 2,909,462 (incorporated by reference), which discusses such acrylic polymers cross-linked with a polyhydroxylated compound containing at least 3 hydroxyl groups; a polyhydroxylated compound contains not more than 8 hydroxyl groups; as another example, the hydrogen atoms of at least 3 hydroxyls are replaced with unsaturated aliphatic radicals containing at least 2 carbon atoms. Radicals can contain from about 2 to about 4 carbon atoms, e.g., vinyls, allyls and other ethylenically unsaturated groups. The unsaturated radicals can themselves contain other substituents, such as methyl. The products sold under the name Carbopol® (Noveon Inc., Ohio, USA) are particularly suitable for use as adjuvants. They are cross-linked with an allyl sucrose or with allyl-pentaerythritol, as to which, mention is made of the products Carbopol® 974P, 934P, and 971P.

As to the copolymers of maleic anhydride and of alkenyl derivative, mention is made of the EMA® products (Monsanto), which are copolymers of maleic anhydride and of ethylene, which may be linear or cross-linked, for example, cross-linked with divinyl ether. Also, reference may be made to U.S. Pat. No. 6,713,068 and Regelson, W. et al., 1960; (incorporated by reference).

Cationic lipids containing a quaternary ammonium salt are described in U.S. Pat. No. 6,713,068, the contents of which are incorporated by reference, can also be used in the methods and compositions of the present invention. Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidylethanolamine; Behr J. P. et al, 1994), to form DMRIE-DOPE.

The total content of components in reconstituted ready-to-inject immunogenic compositions or vaccine compositions of the invention can be used to provide an injection at an isotonic concentration, e.g., within the range of about 100-1200 mOsm, generally within about 250-600 mOsm, and preferably about 330 mOsm.

Dosages of live pathogens, notably *T gondii*, in a freeze-dried stabilized immunogenic compositions or vaccine composition, or in reconstituted ready-to-inject immunogenic compositions or vaccine compositions, can range from about $10^2$ to about $10^7$ CCID$_{50}$/dose.

The reconstituted ready-to-use immunogenic compositions or vaccine compositions can be administered to an animal by injection through the parenteral or mucosal route, preferably intramuscular and subcutaneous. However, administration of such reconstituted ready-to-use immunogenic compositions or vaccine compositions can also comprise intranasal, epicutaneous, topical, or oral administration. The volume of a dose for injection can be from about 0.1 ml to about 2.0 ml, and preferably about 1.0 ml.

The invention will now be further described by way of the following non-limiting Examples, given by way of illustration of various embodiments of the invention and are not meant to limit the present invention in any fashion.

EXAMPLES

For the following examples, "Toxo KO" means an attenuated *Toxoplasma* parasite ("KO" means "knockout") and "Neo KO" means an attenuated *Neospora* parasite. Detailed instructions for producing attenuated/mutated parasite strains may be found in the following documents: U.S. Pat. No. 7,964,185 B2 (to CNRS et al.), which describes construction of attenuated *Toxoplasma gondii* having MIC1 and/or MIC3 genes deletions (referred to as: Toxo mic1 KO, Toxo mic3 KO, and Toxo mic1-3 KO), WO 2014/020291 (to Vitamfero et al.), which describes construction of attenuated *Neospora caninum* having ncMIC1 and/or ncMIC3 genes deletions (referred to as: Neo ncmic1 KO, Neo ncmic3 KO, and Neo ncmic1-3 KO) and WO 2014/020290 A2 (to VitamFero et al.), which describes construction of Neo ncmic3 KO, Neo ncmic1 KO and Neo ncmic1-3 KO strains. Unless otherwise specified, "Toxo KO" refers to the Toxo mic1-3 KO strain and "Neo KO" refers to the Neo ncmic1-3 KO.

Example 1: Lyophilization of Toxo KO Tachyzoites Suspended in an Aqueous Formulation Solution of Formulation F1

A suspension of Toxo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 0.1M trehalose, 0.1M sucrose, 2.5% autoclaved inulin, 0.1M GSH (glutathione), 1% ectoine, 1% proline adjusted at pH 7.4 with sodium hydroxide (formulation F1). The concentration of parasites is $1 \cdot 10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C. Four batches of freeze-dried composition, also called "pastille" or "cake" were produced at separate days. They contained between 4.78 and 4.97% of residual water.

Example 2: Reconstitution of the Lyophilized Composition of Example 1 after Storage for 7 to 22 Days at 4° C., Viability Measurement and In Vivo Study of the Efficacy of the Rehydrated Lyophilized Composition as a Vaccine Before use, freeze-dried samples of the 4 batches produced in the above example were brought back to atmospheric pressure by gentle opening of glass vials after 7 to 22 days storage at 4° C. Dry cakes were resuspended into 1 ml of DMEM (rehydration medium) introduced at a flow rate of 250 µl/second. The viability of resuspended tachyzoites, determined by flow cytometry, was comprised between 3.5 and 67.5%.

An in vivo study was performed to evaluate the efficacy of the 4 batches of freeze-dried tachyzoites as a vaccine against toxoplasmosis. For each batch, 3 to 6 mice were inoculated by intraperitoneal injection at day 0 with a dose of $4 \cdot 10^6$ freeze-dried tachyzoites and one control mouse received the parasite-free freeze-dried bioformulation alone (placebo). The humoral immune response of mice was quantified at day 30 by titration of specific IgG antibodies against *T gondii* in sera. The IgG titer was increased by 333% to 372% for the mice inoculated with the freeze-dried tachyzoites compared to the placebo group. Consecutively to a challenge with *T gondii* RH strain at day 60, the mouse survival rate was comprised between 83% to 100% at day 90, whereas all the mice that received the placebo died after the challenge. Those results confirm the ability of freeze-dried tachyzoites to vaccinate and effectively protect mice against toxoplasmosis.

Example 3: In Vivo Study of the Infectivity of the Tachyzoites of the Rehydrated Lyophilized Composition of Example 2

An in vivo study was performed to evaluate the infectivity of 1 batch of freeze-dried tachyzoites produced in the above example. Two mice were inoculated by intraperitoneal injection at day 0 with a dose of $4 \cdot 10^6$ freeze-dried tachyzoites and sacrificed at day 12. The spleen was removed and crushed. The splenocytes were extracted and added to Human Foreskin Fibroblasts cells in culture. After 9 days, parasites were observed in the culture medium for the 2 mice, confirming the infectivity of freeze-dried tachyzoites.

Example 4: Reconstitution of the Lyophilized Composition of Example 1 after Storage for 60 Days at 4° C., Viability Measurement and In Vivo Study of the Efficacy of the Rehydrated Lyophilized Composition as a Vaccine One batch of freeze-dried samples produced in the above example was tested after 60 days storage at 4° C. The glass vials were brought back to atmospheric pressure by gentle opening of glass vials after 60 days storage. The residual water (moisture content) was 4.2%. Dry cakes were resuspended into 1 ml of DMEM (rehydration medium) introduced at a flow rate of 250 µl/second. The viability of resuspended tachyzoites, determined by flow cytometry, was 9.4%.

An in vivo study was performed to evaluate the efficacy of this batch of freeze-dried tachyzoites as a vaccine against toxoplasmosis. Six mice were inoculated by intraperitoneal injection at day 0 with a dose of $4 \cdot 10^6$ freeze-dried tachyzoites and 2 control mice received the parasite-free freeze-dried bioformulation alone (placebo). The humoral immune response of mice was quantified at day 30 by titration of specific IgG antibodies against *T gondii* in sera. The IgG titer was increased by 270% for the mice inoculated with the freeze-dried tachyzoites compared to the placebo group. Consecutively to a challenge with *T gondii* RH strain at day 60, the mouse survival rate was 50% at day 90, whereas all the mice that received the placebo died after the challenge. Those results confirm the ability of freeze-dried tachyzoites to vaccinate and effectively protect mice against toxoplasmosis after 60 days storage at 4° C.

Example 5: Reconstitution of the Lyophilized Composition of Example 1 after Storage for 60 Days at −20° C., Viability Measurement and In Vivo Study of the Efficacy of the Rehydrated Lyophilized Composition as a Vaccine One batch of freeze-dried samples produced in the above example was tested after 60 days storage at −20° C. The glass vials were brought back to atmospheric pressure by gentle opening of glass vials after 60 days storage. The residual water (moisture content) was 7.0%. Dry cakes were resuspended into 1 ml of DMEM (rehydration medium) introduced at a flow rate of 250 µl/second. The viability of resuspended tachyzoites, determined by flow cytometry, was 10.1%.

An in vivo study was performed to evaluate the efficacy of this batch of freeze-dried tachyzoites as a vaccine against toxoplasmosis. Six mice were inoculated by intraperitoneal injection at day 0 with a dose of $4 \cdot 10^6$ freeze-dried tachyzoites and 1 control mouse received the parasite-free freeze-dried bioformulation alone (placebo). The humoral immune response of mice was quantified at day 30 by titration of specific IgG antibodies against *T gondii* in sera. The IgG titer was increased by 483% for the mice inoculated with the freeze-dried tachyzoites compared to the placebo group. Consecutively to a challenge with *T gondii* RH strain at day 60, the mouse survival rate was 67% at day 90, whereas all the mice that received the placebo died after the challenge. Those results confirm the ability of freeze-dried tachyzoites to vaccinate and effectively protect mice against toxoplasmosis after 60 days storage at −20° C.

Example 6: Lyophilization of Killed Toxo KO Tachyzoites Suspended in the Aqueous Formulation Solution of Formulation F1 (Negative Control)

A suspension of Toxo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 0.1M trehalose, 0.1M sucrose, 2.5% autoclaved inulin, 0.1M GSH (glutathione), 1% ectoine, 1% proline adjusted at pH 7.4 with sodium hydroxide. The concentration of parasites is $1 \cdot 10^7$/ml. This parasite suspension was then placed in a water bath and maintained at 56° C. for 90 minutes to kill the parasites. An aliquot of this suspension was then added to Vero cells in culture to evaluate the infectivity of the parasites. After 5 days, no parasitophorous vacuole or plaque forming unit were observed confirming the death of parasites. One ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C. The freeze-dried composition, also called "pastille" or "cake" contained 4.85% of residual water.

Example 7: Reconstitution of the Lyophilized Composition of the Example 6 and In Vivo Study of the Efficacy of the Rehydrated Lyophilized Composition as a Vaccine (Negative Control)

Before use, freeze-dried samples were brought back to atmospheric pressure by gentle opening of glass vials. Dry cakes were resuspended into 1 ml of DMEM (rehydration medium) introduced at a flow rate of 250 μl/second.

An in vivo study was performed to evaluate the efficacy of the batch of freeze-dried dead tachyzoites as a vaccine against toxoplasmosis. Six mice were inoculated by intraperitoneal injection at day 0 with a dose of $4 \cdot 10^6$ freeze-dried dead tachyzoites. The humoral immune response of mice was quantified at day 30 by titration of specific IgG antibodies against T gondii in sera. The IgG titer was increased by 206%. Consecutively to a challenge with T gondii RH strain at day 60, 5 of the 6 mice died leading to a survival rate of 17% at day 90. Those results confirm the inability of freeze-dried dead tachyzoites to vaccinate and effectively protect mice against toxoplasmosis.

Example 8: Lyophilization of Toxo KO Tachyzoites Suspended in an Aqueous Formulation Solution of Formulation F2

A suspension of Toxo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 0.1M trehalose and 5% ascorbic acid adjusted at pH 7.4 with sodium hydroxide (formulation F2). The concentration of parasites is $1 \cdot 10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C. Two batches of freeze-dried composition, also called "pastille" or "cake" were produced at separate days. They contained between 9.6 and 9.8% of residual water.

Example 9: Reconstitution of the Lyophilized Composition of Example 8 after Storage for 7 to 8 Days at 4° C., Viability Measurement and In Vivo Study of the Efficacy of the Rehydrated Lyophilized Composition as a Vaccine Before use, freeze-dried samples of the 2 batches produced in the above example were brought back to atmospheric pressure by gentle opening of glass vials after 7 to 8 days storage at 4° C. Dry cakes were resuspended into 1 ml of DMEM (rehydration medium) introduced at a flow rate of 250 μl/second. The viability of resuspended tachyzoites, determined by flow cytometry, was comprised between 17% and 66.3%.

An in vivo study was performed to evaluate the efficacy of the 2 batches of freeze-dried tachyzoites as a vaccine against toxoplasmosis. For each batch, 3 to 6 mice were inoculated by intraperitoneal injection at day 0 with a dose of $4 \cdot 10^6$ freeze-dried tachyzoites and one control mouse received the parasite-free freeze-dried bioformulation alone (placebo). The humoral immune response of mice was quantified at day 30 by titration of specific IgG antibodies against T gondii in sera. The IgG titer was increased by 256% to 286% for the mice inoculated with the freeze-dried tachyzoites compared to the placebo group. Consecutively to a challenge with T gondii RH strain at day 60, the mouse survival rate was comprised between 67% to 100% at day 90, whereas all the mice that received the placebo died after the challenge. Those results confirm the ability of freeze-dried tachyzoites to vaccinate and effectively protect mice against toxoplasmosis.

Example 10: Reconstitution of the Lyophilized Composition of Example 8 after Storage for 60 Days at 4° C., Viability Measurement and In Vivo Study of the Efficacy of the Rehydrated Lyophilized Composition as a Vaccine One batch of freeze-dried samples produced in the above example was tested after 60 days storage at 4° C. The glass vials were brought back to atmospheric pressure by gentle opening of glass vials after 60 days storage. The residual water (moisture content) was 10.7%. Dry cakes were resuspended into 1 ml of DMEM (rehydration medium) introduced at a flow rate of 250 μl/second. The viability of resuspended tachyzoites, determined by flow cytometry, was 9.8%.

An in vivo study was performed to evaluate the efficacy of this batch of freeze-dried tachyzoites as a vaccine against toxoplasmosis. Six mice were inoculated by intraperitoneal injection at day 0 with a dose of $4 \cdot 10^6$ freeze-dried tachyzoites and 2 control mice received the parasite-free freeze-dried bioformulation alone (placebo). The humoral immune response of mice was quantified at day 30 by titration of specific IgG antibodies against *T gondii* in sera. The IgG titer was increased by 410% for the mice inoculated with the freeze-dried tachyzoites compared to the placebo group. Consecutively to a challenge with *T gondii* RH strain at day 60, the mouse survival rate was 83% at day 90, whereas all the mice that received the placebo died after the challenge. Those results confirm the ability of freeze-dried tachyzoites to vaccinate and effectively protect mice against toxoplasmosis after 60 days storage at 4° C.

Example 11: Lyophilization of Toxo KO Tachyzoites Suspended in an Aqueous Formulation Solution of Formulation F3

A suspension of Toxo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 0.1M trehalose, 0.1M sucrose, 5% inulin (formulation F3). The concentration of parasites is $1 \cdot 10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C. Two batches of freeze-dried composition, also called "pastille" or "cake" were produced at separate days. They contained between 5.0 and 6.9% of residual water.

Example 12: Reconstitution of the Lyophilized Composition of Example 11 after Storage for 7 to 8 Days at 4° C., Viability Measurement and In Vivo Study of the Efficacy of the Rehydrated Lyophilized Composition as a Vaccine Before use, freeze-dried samples of the 2 batches produced in the above example were brought back to atmospheric pressure by gentle opening of glass vials after 7 to 8 days storage at 4° C. Dry cakes were resuspended into 1 ml of DMEM (rehydration medium) introduced at a flow rate of 250 μl/second. The viability of resuspended tachyzoites, determined by flow cytometry, was comprised between 18.9% and 72.5%.

An in vivo study was performed to evaluate the efficacy of the 2 batches of freeze-dried tachyzoites as a vaccine against toxoplasmosis. For each batch, 3 to 6 mice were inoculated by intraperitoneal injection at day 0 with a dose of $4 \cdot 10^6$ freeze-dried tachyzoites and one control mouse received the parasite-free freeze-dried bioformulation alone (placebo). The humoral immune response of mice was quantified at day 30 by titration of specific IgG antibodies against *T gondii* in sera. The IgG titer was increased by 101% to 246% for the mice inoculated with the freeze-dried tachyzoites compared to the placebo group. Consecutively to a challenge with *T gondii* RH strain at day 60, the mouse survival rate was comprised between 67% to 100% at day 90, whereas all the mice that received the placebo died after the challenge. Those results confirm the ability of freeze-dried tachyzoites to vaccinate and effectively protect mice against toxoplasmosis.

Example 13: Reconstitution of the Lyophilized Composition of Example 11 after Storage for 60 Days at 4° C., Viability Measurement and In Vivo Study of the Efficacy of the Rehydrated Lyophilized Composition as a Vaccine One batch of freeze-dried samples produced in the above example was tested after 60 days storage at 4° C. The glass vials were brought back to atmospheric pressure by gentle opening of glass vials after 60 days storage. The residual water (moisture content) was 7.0%. Dry cakes were resuspended into 1 ml of DMEM (rehydration medium) introduced at a flow rate of 250 μl/second. The viability of resuspended tachyzoites, determined by flow cytometry, was 5.2%.

An in vivo study was performed to evaluate the efficacy of this batch of freeze-dried tachyzoites as a vaccine against toxoplasmosis. Six mice were inoculated by intraperitoneal injection at day 0 with a dose of $4 \cdot 10^6$ freeze-dried tachyzoites and 2 control mice received the parasite-free freeze-dried bioformulation alone (placebo). The humoral immune response of mice was quantified at day 30 by titration of specific IgG antibodies against *T gondii* in sera. The IgG titer was increased by 255% for the mice inoculated with the freeze-dried tachyzoites compared to the placebo group. Consecutively to a challenge with *T gondii* RH strain at day 60, the mouse survival rate was 67% at day 90, whereas all the mice that received the placebo died after the challenge. Those results confirm the ability of freeze-dried tachyzoites to vaccinate and effectively protect mice against toxoplasmosis after 60 days storage at 4° C.

Example 14: Lyophilization of Toxo KO Tachyzoites Suspended in an Aqueous Formulation Solution of formulation F4

A suspension of Toxo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 0.2M trehalose, 0.15M sucrose, 0.1M GSH (glutathione), 1% ectoine, 1% proline adjusted at pH 7.4 with sodium hydroxide (formulation F4). The concentration of parasites is $1 \cdot 10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C. Two batches of freeze-dried composition, also called "pastille" or "cake" were produced at separate days. They contained between 5.7 and 7.0% of residual water.

Example 15: Reconstitution of the Lyophilized Composition of Example 14 after Storage for 7 to 8 Days at 4° C., Viability Measurement and In Vivo Study of the Efficacy of the Rehydrated Lyophilized Composition as a Vaccine Before use, freeze-dried samples of the 2 batches produced in the above example were brought back to atmospheric pressure by gentle opening of glass vials after 7 to 8 days storage at 4° C. Dry cakes were resuspended into 1 ml of DMEM (rehydration medium) introduced at a flow rate of 250 µl/second. The viability of resuspended tachyzoites, determined by flow cytometry, was comprised between 11.2% and 72.6%.

An in vivo study was performed to evaluate the efficacy of the 2 batches of freeze-dried tachyzoites as a vaccine against toxoplasmosis. For each batch, 3 to 6 mice were inoculated by intraperitoneal injection at day 0 with a dose of $4 \cdot 10^6$ freeze-dried tachyzoites and one control mouse received the parasite-free freeze-dried bioformulation alone (placebo). The humoral immune response of mice was quantified at day 30 by titration of specific IgG antibodies against *T gondii* in sera. The IgG titer was increased by 314% to 337% for the mice inoculated with the freeze-dried tachyzoites compared to the placebo group. Consecutively to a challenge with *T gondii* RH strain at day 60, the mouse survival rate was comprised between 83% to 100% at day 90, whereas all the mice that received the placebo died after the challenge. Those results confirm the ability of freeze-dried tachyzoites to vaccinate and effectively protect mice against toxoplasmosis.

Example 16: Reconstitution of the Lyophilized Composition of Example 14 after Storage for 60 Days at 4° C., Viability Measurement and In Vivo Study of the Efficacy of the Rehydrated Lyophilized Composition as a Vaccine One batch of freeze-dried samples produced in the above example was tested after 60 days storage at 4° C. The glass vials were brought back to atmospheric pressure by gentle opening of glass vials after 60 days storage. The residual water (moisture content) was 5.8%. Dry cakes were resuspended into 1 ml of DMEM (rehydration medium) introduced at a flow rate of 250 µl/second. The viability of resuspended tachyzoites, determined by flow cytometry, was 4.2%.

An in vivo study was performed to evaluate the efficacy of this batch of freeze-dried tachyzoites as a vaccine against toxoplasmosis. Six mice were inoculated by intraperitoneal injection at day 0 with a dose of $4 \cdot 10^6$ freeze-dried tachyzoites and 2 control mice received the parasite-free freeze-dried bioformulation alone (placebo). The humoral immune response of mice was quantified at day 30 by titration of specific IgG antibodies against *T gondii* in sera. The IgG titer was increased by 390% for the mice inoculated with the freeze-dried tachyzoites compared to the placebo group. Consecutively to a challenge with *T gondii* RH strain at day 60, the mouse survival rate was 83% at day 90, whereas all the mice that received the placebo died after the challenge. Those results confirm the ability of freeze-dried tachyzoites to vaccinate and effectively protect mice against toxoplasmosis after 60 days storage at 4° C.

Example 17: Lyophilization of Toxo KO Tachyzoites Suspended in an Aqueous Formulation Solution of Formulation F5

A suspension of Toxo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 10% DMSO (i.e. dimethyl sulfoxide) (formulation F5). The concentration of parasites is $1 \cdot 10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C. One batch of freeze-dried composition, also called "pastille" or "cake" was produced.

Example 18: Reconstitution of the Lyophilized Composition of Example 17 after Storage for 7 Days at 4° C., Viability Measurement and In Vivo Study of the Efficacy of the Rehydrated Lyophilized Composition as a Vaccine Before use, freeze-dried sample of the batch produced in the above example was brought back to atmospheric pressure by gentle opening of glass vials after 7 days storage at 4° C. Dry cake was resuspended into 1 ml of DMEM (rehydration medium) introduced at a flow rate of 250 µl/second. The viability of resuspended tachyzoites, determined by flow cytometry, was 57.6%.

An in vivo study was performed to evaluate the efficacy of the batch of freeze-dried tachyzoites as a vaccine against toxoplasmosis. Three mice were inoculated by intraperitoneal injection at day 0 with a dose of $4 \cdot 10^6$ freeze-dried tachyzoites and one control mouse received the parasite-free freeze-dried bioformulation alone (placebo). The humoral immune response of mice was quantified at day 30 by titration of specific IgG antibodies against *T gondii* in sera. The IgG titer was increased by 94% for the mice inoculated with the freeze-dried tachyzoites compared to the placebo group. Consecutively to a challenge with *T gondii* RH strain at day 60, the mouse survival rate was 67% at day 90, whereas all the mice that received the placebo died after the challenge. Those results confirm the ability of freeze-dried tachyzoites to vaccinate and effectively protect mice against toxoplasmosis.

Example 19: Lyophilization of Toxo KO Tachyzoites Suspended in an Aqueous Formulation Solution of Formulation F6

A suspension of Toxo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 0.1M trehalose and 1 mg/ml EGCG (Epigallocatechin gallate) (formulation F6). The concentration of parasites is $1 \cdot 10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C. One batch of freeze-dried composition, also called "pastille" or "cake" was produced and contained 10.4% of residual water.

Example 20: Reconstitution of the Lyophilized Composition of Example 19 after Storage for 7 Days at 4° C., Viability Measurement and In Vivo Study of the Efficacy of the Rehydrated Lyophilized Composition as a Vaccine Before use, freeze-dried sample of the batch produced in the above example was brought back to atmospheric pressure by gentle opening of glass vials after 7 days storage at 4° C. Dry cake was resuspended into 1 ml of DMEM (rehydration medium) introduced at a flow rate of 250 µl/second. The viability of resuspended tachyzoites, determined by flow cytometry, was 30.8%.

An in vivo study was performed to evaluate the efficacy of the batch of freeze-dried tachyzoites as a vaccine against toxoplasmosis. Three mice were inoculated by intraperitoneal injection at day 0 with a dose of $4 \cdot 10^6$ freeze-dried tachyzoites and one control mouse received the parasite-free freeze-dried bioformulation alone (placebo). The humoral immune response of mice was quantified at day 30 by titration of specific IgG antibodies against *T gondii* in sera. The IgG titer was increased by 342% for the mice inoculated with the freeze-dried tachyzoites compared to the placebo group. Consecutively to a challenge with *T gondii* RH strain at day 60, the mouse survival rate was 67% at day 90, whereas all the mice that received the placebo died after the challenge. Those results confirm the ability of freeze-dried tachyzoites to vaccinate and effectively protect mice against toxoplasmosis.

Example 21: Lyophilization of Toxo KO Tachyzoites Suspended in an Aqueous Formulation Solution of Formulation F7

A suspension of Toxo KO tachyzoites in a culture medium, freshly egressed from host cells, was centrifuged for 10 min at 1,500 g. The supernatant was removed and the pellet resuspended in an aqueous formulation solution composed of PBS (i.e. Phosphate Buffered Saline) complemented with 0.1M trehalose, 0.1M sucrose, 2.5% autoclaved inulin, 0.1M GSH (glutathione), 1% ectoine, 1% proline adjusted at pH 7.4 with sodium hydroxide (formulation F7). The concentration of parasites is $1 \cdot 10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C. One batch of freeze-dried composition, also called "pastille" or "cake" was produced and contained 4.0% of residual water.

Example 22: Reconstitution of the Lyophilized Composition of Example 21 after Storage for 7 Days at 4° C., Viability Measurement and In Vivo Study of the Efficacy of the Rehydrated Lyophilized Composition as a Vaccine Before use, freeze-dried sample of the batch produced in the above example was brought back to atmospheric pressure by gentle opening of glass vials after 7 days storage at 4° C. Dry cake was resuspended into 1 ml of DMEM (rehydration medium) introduced at a flow rate of 250 µl/second. The viability of resuspended tachyzoites, determined by flow cytometry, was 64.6%.

An in vivo study was performed to evaluate the efficacy of the batch of freeze-dried tachyzoites as a vaccine against toxoplasmosis. Three mice were inoculated by intraperitoneal injection at day 0 with a dose of $4 \cdot 10^6$ freeze-dried tachyzoites and one control mouse received the parasite-free freeze-dried bioformulation alone (placebo). The humoral immune response of mice was quantified at day 30 by titration of specific IgG antibodies against *T gondii* in sera. The IgG titer was increased by 337% for the mice inoculated with the freeze-dried tachyzoites compared to the placebo group. Consecutively to a challenge with *T gondii* RH strain at day 60, the mouse survival rate was 67% at day 90, whereas all the mice that received the placebo died after the challenge. Those results confirm the ability of freeze-dried tachyzoites to vaccinate and effectively protect mice against toxoplasmosis.

Example 23: Lyophilization of Toxo KO Tachyzoites Suspended in the Aqueous Formulation Solution of Formulation F1, after a First Treatment by Distilled Water with 2.5% Trehalose A suspension of Toxo KO tachyzoites in a culture medium, freshly egressed from host cells, was centrifuged for 10 min at 1,500 g. The supernatant was removed and the pellet resuspended in a medium composed of DMEM (i.e. Dulbecco's Modified Eagle Medium) complemented with 0.1M trehalose, 0.1M sucrose, 2.5% autoclaved inulin, 0.1M GSH (glutathione), 1% ectoine, 1% proline adjusted at pH 7.4 with sodium hydroxide. After 30 minutes at 37° C., the suspension was centrifuged for 10 min at 1,500 g. The supernatant was removed and the pellet resuspended in distilled water added with 2.5% trehalose. After 1 h at 37° C., the suspension was centrifuged for 10 min at 1,500 g. The supernatant was removed and the pellet resuspended in an aqueous formulation solution composed of DMEM (i.e. Dulbecco's Modified Eagle Medium) complemented with 0.1M trehalose, 0.1M sucrose, 2.5% autoclaved inulin, 0.1M GSH (glutathione), 1% ectoine, 1% proline adjusted at pH 7.4 with sodium hydroxide. The concentration of parasites is $1 \cdot 10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C. One batch of freeze-dried composition, also called "pastille" or "cake" was produced and contained 4.8% of residual water.

Example 24: Reconstitution of the Lyophilized Composition of Example 23 after Storage for 7 Days at 4° C., Viability Measurement and In Vivo Study of the Efficacy of the Rehydrated Lyophilized Composition as a Vaccine Before use, freeze-dried sample of the batch produced in the above example was brought back to atmospheric pressure by gentle opening of glass vials after 7 days storage at 4° C. Dry cake was resuspended into 1 ml of DMEM (rehydration medium) introduced at a flow rate of 250 µl/second. The viability of resuspended tachyzoites, determined by flow cytometry, was 55.0%.

An in vivo study was performed to evaluate the efficacy of the batch of freeze-dried tachyzoites as a vaccine against toxoplasmosis. Three mice were inoculated by intraperitoneal injection at day 0 with a dose of $4 \cdot 10^6$ freeze-dried tachyzoites and one control mouse received the parasite-free freeze-dried bioformulation alone (placebo). The humoral immune response of mice was quantified at day 30 by titration of specific IgG antibodies against *T gondii* in sera. The IgG titer was increased by 226% for the mice inoculated with the freeze-dried tachyzoites compared to the placebo group. Consecutively to a challenge with *T gondii* RH strain at day 60, the mouse survival rate was 33% at day 90, whereas all the mice that received the placebo died after the challenge. Those results confirm the ability of freeze-dried tachyzoites to vaccinate and effectively protect mice against toxoplasmosis.

Example 25: Lyophilization of Toxo KO Tachyzoites Suspended in the Aqueous Formulation Solution of Formulation F5 by a Second Process of Lyophilization (Counterexample 1)

A suspension of Toxo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 10% DMSO (i.e. dimethyl sulfoxide). The concentration of parasites is $2.5 \cdot 10^7$/ml. 0.2 ml of such a parasite suspension was dispensed in 2 ml glass vials that were placed onto the shelf of a freeze-dryer. Samples were kept freezing at atmospheric pressure for 4 h at a temperature lowered from 20° C. to −55° C. according to a kinetic of −1° C. per minute. At the end of the freezing period, the freeze-drying chamber was rendered inert with nitrogen gas before starting the drying at −40° C. for 4 h. The freeze-dryer shelf temperature was then increased from −40° C. to +5° C. at a rate of 0.0625° C. per minute with a 4 h plateau upon reaching every 15° C. increase. The pressure was maintained below 50 Pa during all the drying process. At the end of the freeze-drying process, the glass vials were mechanically sealed. The vacuum was then gently broken and the samples stored at 4° C. The freeze-dried composition is also called "pastille" or "cake".

Example 26: Reconstitution of the Lyophilized Composition of Example 25 after Storage for 7 Days at 4° C., Viability Measurement and In Vivo Study of the Efficacy of the Rehydrated Lyophilized Composition as a Vaccine (Counterexample 1)

Before use, freeze-dried sample of the batch produced in the above example was brought back to atmospheric pressure by gentle opening of glass vials after 7 days storage at 4° C. Dry cake was resuspended into 0.5 ml of DMEM (rehydration medium) introduced at a flow rate of 250 µl/second. The viability of resuspended tachyzoites, determined by flow cytometry, was 30.0%.

An in vivo study was performed to evaluate the efficacy of the batch of freeze-dried tachyzoites as a vaccine against toxoplasmosis. Five mice were inoculated by intraperitoneal injection at day 0 with a dose of $4 \cdot 10^6$ freeze-dried tachyzoites. The humoral immune response of mice was quantified at day 30 by titration of specific IgG antibodies against *T gondii* in sera. The IgG titer was increased by 83% at day 30 compared to day 0. Consecutively to a challenge with *T gondii* RH strain at day 60, all the mice died before day 90. Those results show that viable parasites can lead to an ineffective vaccine and suggest that freeze-dried tachyzoites have to be viable and infectious to protect mice against toxoplasmosis.

Example 27: Lyophilization of Toxo KO Suspended in the Aqueous Formulation Solution of Formulation F2 by a Second Process of Lyophilization (Counterexample 2)

A suspension of Toxo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 0.1M trehalose and 5% ascorbic acid.

The concentration of parasites is $2.5 \cdot 10^7$/ml. 0.2 ml of such a parasite suspension was dispensed in 2 ml glass vials that were placed onto the shelf of a freeze-dryer. Samples were kept freezing at atmospheric pressure for 4 h at a temperature lowered from 20° C. to −55° C. according to a kinetic of −1° C. per minute. At the end of the freezing period, the freeze-drying chamber was rendered inert with nitrogen gas before starting the drying at −40° C. for 4 h. The freeze-dryer shelf temperature was then increased from −40° C. to +5° C. at a rate of 0.0625° C. per minute with a 4 h plateau upon reaching every 15° C. increase. The pressure was maintained below 50 Pa during all the drying process. At the end of the freeze-drying process, the glass vials were mechanically sealed. The vacuum was then gently broken and the samples stored at 4° C. The freeze-dried composition is also called "pastille" or "cake".

Example 28: Reconstitution of the Lyophilized Composition of Example 27 after Storage for 7 Days at 4° C., Viability Measurement and In Vivo Study of the Efficacy of the Rehydrated Lyophilized Composition as a Vaccine (Counterexample 2)

Before use, freeze-dried sample of the batch produced in the above example was brought back to atmospheric pressure by gentle opening of glass vials after 7 days storage at 4° C. Dry cake was resuspended into 0.5 ml of DMEM (rehydration medium) introduced at a flow rate of 250 μl/second. The viability of resuspended tachyzoites, determined by flow cytometry, was 68.0%.

An in vivo study was performed to evaluate the efficacy of the batch of freeze-dried tachyzoites as a vaccine against toxoplasmosis. Two mice were inoculated by intraperitoneal injection at day 0 with a dose of $4 \cdot 10^6$ freeze-dried tachyzoites. The humoral immune response of mice was quantified at day 30 by titration of specific IgG antibodies against *T gondii* in sera. The IgG titer was increased by 219% at day 30 compared to day 0. Consecutively to a challenge with *T gondii* RH strain at day 60, all the mice died before day 90. Those results show that viable parasites can lead to a ineffective vaccine and suggest that freeze-dried tachyzoites have to be viable and infectious to protect mice against toxoplasmosis.

Example 29: Lyophilization of Toxo KO Tachyzoites Suspended in the Aqueous Formulation Solution of Formulation F6 by a Second Process of Lyophilization (Counterexample 3)

A suspension of Toxo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 0.1M trehalose and 1 mg/ml EGCG (Epigallocatechin gallate). The concentration of parasites is $2.5 \cdot 10^7$/ml. 0.2 ml of such a parasite suspension was dispensed in 2 ml glass vials that were placed onto the shelf of a freeze-dryer. Samples were kept freezing at atmospheric pressure for 4 h at a temperature lowered from 20° C. to −55° C. according to a kinetic of −1° C. per minute. At the end of the freezing period, the freeze-drying chamber was rendered inert with nitrogen gas before starting the drying at −40° C. for 4 h. The freeze-dryer shelf temperature was then increased from −40° C. to +5° C. at a rate of 0.0625° C. per minute with a 4 h plateau upon reaching every 15° C. increase. The pressure was maintained below 50 Pa during all the drying process. At the end of the freeze-drying process, the glass vials were mechanically sealed. The vacuum was then gently broken and the samples stored at 4° C. The freeze-dried composition is also called "pastille" or "cake".

Example 30: Reconstitution of the Lyophilized Composition of Example 29 after Storage for 7 Days at 4° C., Viability Measurement and In Vivo Study of the Efficacy of the Rehydrated Lyophilized Composition as a Vaccine (Counterexample 3)

Before use, freeze-dried sample of the batch produced in the above example was brought back to atmospheric pressure by gentle opening of glass vials after 7 days storage at 4° C. Dry cake was resuspended into 0.5 ml of DMEM (rehydration medium) introduced at a flow rate of 250 μl/second. The viability of resuspended tachyzoites, determined by flow cytometry, was 77.7%.

An in vivo study was performed to evaluate the efficacy of the batch of freeze-dried tachyzoites as a vaccine against toxoplasmosis. Five mice were inoculated by intraperitoneal injection at day 0 with a dose of $4 \cdot 10^6$ freeze-dried tachyzoites. The humoral immune response of mice was quantified at day 30 by titration of specific IgG antibodies against *T gondii* in sera. The IgG titer was increased by 186% at day 30 compared to day 0. Consecutively to a challenge with *T gondii* RH strain at day 60, all the mice died before day 90. Those results show that viable parasites can lead to a ineffective vaccine and suggest that freeze-dried tachyzoites have to be viable and infectious to protect mice against toxoplasmosis.

Example 31: Lyophilization of Toxo KO Tachyzoites Suspended in an Aqueous Formulation Solution of Formulation F8

A suspension of Toxo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 0.1M trehalose, 0.1M sucrose, 2.5% autoclaved inulin, 0.1M GSH (glutathione), 1% ectoine, 1% proline, 0.1% PLURONIC F68 adjusted at pH 7.4 with sodium hydroxide (formulation F8). The concentration of parasites is $1 \cdot 10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C.

Example 32: Lyophilization of Toxo KO Tachyzoites Suspended in an Aqueous Formulation Solution of Formulation F9

A suspension of Toxo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 0.1M trehalose, 0.1M sucrose, 2.5% autoclaved inulin, 0.1M GSH (glutathione), 1% ectoine, 1% proline, 1% polyvinylpyrrolidone (PVP-40) adjusted at pH 7.4 with sodium hydroxide (formulation F9). The concentration of parasites is $1 \cdot 10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C.

Example 33: Lyophilization of Toxo KO Tachyzoites Suspended in an Aqueous Formulation Solution of Formulation F10

A suspension of Toxo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 0.1M trehalose, 0.1M sucrose, 2.5% autoclaved inulin, 0.1M GSH (glutathione), 1% ectoine, 1% proline, 1% polyethylene glycol (PEG-300) adjusted at pH 7.4 with sodium hydroxide (formulation F10). The concentration of parasites is $1 \cdot 10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C.

Example 34: Lyophilization of Toxo KO Tachyzoites Suspended in an Aqueous Formulation Solution of Formulation F11

A suspension of Toxo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 0.1M trehalose, 0.1M sucrose, 2.5% autoclaved inulin, 0.1M GSH (glutathione), 1% ectoine, 1% proline, 2% sodium alginate adjusted at pH 7.4 with sodium hydroxide (formulation F11). The concentration of parasites is $1 \cdot 10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C.

Example 35: Lyophilization of Toxo KO Tachyzoites Suspended in an Aqueous Formulation Solution of Formulation F12

A suspension of Toxo KO tachyzoites in a culture medium, freshly egressed from host cells, was centrifuged for 10 min at 1,500 g. The supernatant was removed and the pellet resuspended in an aqueous formulation solution composed of PBS (i.e. Phosphate Buffered Saline) complemented with 0.1M trehalose, 0.1M sucrose, 2.5% autoclaved inulin and 5% gelatin (formulation F12). The concentration of parasites is $1 \cdot 10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C.

Example 36: Lyophilization of Toxo KO Tachyzoites Suspended in an Aqueous Formulation Solution of Formulation F13

A suspension of Toxo KO tachyzoites in a culture medium, freshly egressed from host cells, was centrifuged for 10 min at 1,500 g. The supernatant was removed and the pellet resuspended in an aqueous formulation solution composed of PBS (i.e. Phosphate Buffered Saline) complemented with 30% trehalose, 5% gelatin and 0.02% PLURONIC F68 (formulation F13). The concentration of parasites is $1 \cdot 10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C.

Example 37: Lyophilization of Neo KO Tachyzoites Suspended in an Aqueous Formulation Solution of Formulation F8

A suspension of Neo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 0.1M trehalose, 0.1M sucrose, 2.5% autoclaved inulin, 0.1M GSH (glutathione), 1% ectoine, 1% proline, 0.1% PLURONIC F68 adjusted at pH 7.4 with sodium hydroxide. The concentration of parasites is $1 \cdot 10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C.

Example 38: Lyophilization of Neo KO Tachyzoites Suspended in an Aqueous Formulation Solution of Formulation F1

A suspension of Neo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 0.1M trehalose, 0.1M sucrose, 2.5% autoclaved inulin, 0.1M GSH (glutathione), 1% ectoine, 1% proline, adjusted at pH 7.4 with sodium hydroxide. The concentration of parasites is $1 \cdot 10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C. The freeze-dried composition, also called "pastille" or "cake" contained 5.71% of residual water.

Example 38 Bis: Reconstitution of the Lyophilized Composition of Example 38 after Storage for 7 Days at 4° C. and Viability Measurement of the Rehydrated Lyophilized Composition Before use, freeze-dried sample of the batch produced in the above example was brought back to atmospheric pressure by gentle opening of glass vials after 7 days storage at 4° C. Dry cake was resuspended into 1 ml of DMEM (rehydration medium) introduced at a flow rate of 250 μl/second. The viability of resuspended tachyzoites, determined by flow cytometry, was 8.5%.

Example 39: Lyophilization of Neo KO Tachyzoites Suspended in an Aqueous Formulation Solution of Formulation F3

A suspension of Neo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 0.1M trehalose, 0.1M sucrose and 5% inulin. The concentration of parasites is $1 \cdot 10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C. The freeze-dried composition, also called "pastille" or "cake" contained 5.95% of residual water.

Example 39 Bis: Reconstitution of the Lyophilized Composition of Example 39 after Storage for 7 Days at 4° C. and Viability Measurement of the Rehydrated Lyophilized Composition Before use, freeze-dried sample of the batch produced in the above example was brought back to atmospheric pressure by gentle opening of glass vials after 7 days storage at 4° C. Dry cake was resuspended into 1 ml of DMEM (rehydration medium) introduced at a flow rate of 250

μl/second. The viability of resuspended tachyzoites, determined by flow cytometry, was 5.7%.

Example 40: Lyophilization of Neo KO Tachyzoites Suspended in an Aqueous Formulation Solution of Formulation F3

A suspension of Neo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 0.1M trehalose, 0.1M sucrose and 5% autoclaved inulin. The concentration of parasites is $1 \cdot 10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C.

Example 40 Bis: Lyophilization of Neo KO Tachyzoites Suspended in an Aqueous Formulation Solution of Formulation F2

A suspension of Neo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 0.1M trehalose and 5% ascorbic acid adjusted at pH 7.4 with sodium hydroxide. The concentration of parasites is $1 \cdot 10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C. The freeze-dried composition, also called "pastille" or "cake" contained 9.08% of residual water.

Example 40 Ter: Reconstitution of the Lyophilized Composition of Example 40 Bis after Storage for 7 Days at 4° C. and Viability Measurement of the Rehydrated Lyophilized Composition Before use, freeze-dried sample of the batch produced in the above example was brought back to atmospheric pressure by gentle opening of glass vials after 7 days storage at 4° C. Dry cake was resuspended into 1 ml of DMEM (rehydration medium) introduced at a flow rate of 250 μl/second. The viability of resuspended tachyzoites, determined by flow cytometry, was 11.7%.

Example 41: Lyophilization of Neo KO Tachyzoites Suspended in an Aqueous Formulation Solution of Formulation F14

A suspension of Neo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 0.1M trehalose, 0.1M sucrose and 5% autoclaved inulin (formulation F14). The concentration of parasites is $1 \cdot 10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C.

Example 41 Bis: Lyophilization of Neo KO Tachyzoites Suspended in an Aqueous Formulation Solution of Formulation F4

A suspension of Neo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 0.2M trehalose, 0.15M sucrose, 0.1M GSH (glutathione), 1% ectoine, 1% proline adjusted at pH 7.4 with sodium hydroxide. The concentration of parasites is $1 \cdot 10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C. The freeze-dried composition, also called "pastille" or "cake" contained 5.96% of residual water.

Example 41 Ter: Reconstitution of the Lyophilized Composition of Example 41 Bis after Storage for 7 Days at 4° C. and Viability Measurement of the Rehydrated Lyophilized Composition Before use, freeze-dried sample of the batch produced in the above example was brought back to atmospheric pressure by gentle opening of glass vials after 7 days storage at 4° C. Dry cake was resuspended into 1 ml of DMEM (rehydration medium) introduced at a flow rate of 250 μl/second. The viability of resuspended tachyzoites, determined by flow cytometry, was 10.0%.

Example 42: Lyophilization of Neo KO Tachyzoites Suspended in an Aqueous Formulation Solution of Formulation F9

A suspension of Neo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 0.1M trehalose, 0.1M sucrose, 2.5% autoclaved inulin, 0.1M GSH (glutathione), 1% ectoine, 1% proline, 1% polyvinylpyrrolidone (PVP-40) adjusted at pH 7.4 with sodium hydroxide. The concentration of parasites is $1·10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C.

Example 43: Lyophilization of Neo KO Tachyzoites Suspended in an Aqueous Formulation Solution of Formulation F10

A suspension of Neo KO tachyzoites in a culture medium, freshly egressed from host cells, was centrifuged for 10 min at 1,500 g. The supernatant was removed and the pellet resuspended in an aqueous formulation solution composed of DMEM (i.e. Dulbecco's Modified Eagle Medium) complemented with 0.1M trehalose, 0.1M sucrose, 2.5% autoclaved inulin, 0.1M GSH (glutathione), 1% ectoine, 1% proline, 1% polyethylene glycol (PEG-300) adjusted at pH 7.4 with sodium hydroxide. The concentration of parasites is $1·10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C.

Example 44: Lyophilization of Neo KO Tachyzoites Suspended in an Aqueous Formulation Solution of Formulation F12

A suspension of Neo KO tachyzoites in a culture medium, freshly egressed from host cells, was centrifuged for 10 min at 1,500 g. The supernatant was removed and the pellet resuspended in an aqueous formulation solution composed of PBS (i.e. Phosphate Buffered Saline) complemented with 0.1M trehalose, 0.1M sucrose, 2.5% autoclaved inulin, 5% gelatin. The concentration of parasites is $1·10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C.

Example 45: Lyophilization of Neo KO Tachyzoites Suspended in an Aqueous Formulation Solution of Formulation F13

A suspension of Neo KO tachyzoites in a culture medium, freshly egressed from host cells, was centrifuged for 10 min at 1,500 g. The supernatant was removed and the pellet resuspended in an aqueous formulation solution composed of PBS (i.e. Phosphate Buffered Saline) complemented with 30% trehalose, 5% gelatin and 0.02% PLURONIC F68. The concentration of parasites is $1·10^7$/ml. After an equilibration period of 1 h, 1 ml of such a parasite suspension was dispensed in 10 ml glass vials that were placed onto the shelf of a freeze-dryer. Samples were kept freezing at atmospheric pressure for 23 h at a temperature lowered from 20° C. to −75° C. according to a kinetic of −1° C. per minute. The primary drying was performed at −55° C. for 20 h with a pressure maintained between 30 and 80 Pa during the first 7 hours and then below 2 Pa. For the secondary drying, the pressure was maintained below 2 Pa and the freeze-dryer shelf temperature was increased from −55° C. to +5° C. at a rate of 0.0625° C. per minute with a 1 h plateau upon reaching every 15° C. increase. Secondary drying was completed by maintaining samples at +5° C. for 4 h at a pressure below 2 Pa. At the end of the freeze-drying process, the glass vials were mechanically sealed. The vacuum was then gently broken and the samples stored at 4° C.

Example 46: Lyophilization of *Neospora caninum* Tachyzoites Suspended in an Aqueous Formulation Solution of Formulation F1

A suspension of a live attenuated strain of *Neospora caninum* tachyzoites in a culture medium, freshly egressed from host cells, is centrifuged for 10 min at 1,500 g. The supernatant is removed and the pellet resuspended in an aqueous formulation solution composed of DMEM (i.e. Dulbecco's Modified Eagle Medium) complemented with 0.1M trehalose, 0.1M sucrose, 2.5% autoclaved inulin, 0.1M GSH (glutathione), 1% ectoine, 1% proline, adjusted at pH 7.4 with sodium hydroxide. The concentration of parasites is $1·10^7$/ml. After an equilibration period of 1 h, 1 ml of such a parasite suspension is dispensed in 10 ml glass vials that are placed onto the shelf of a freeze-dryer. Samples are kept freezing at atmospheric pressure for 23 h at a temperature lowered from 20° C. to −75° C. according to a kinetic of −1° C. per minute. The primary drying is performed at −55° C. for 20 h with a pressure maintained between 30 and 80 Pa during the first 7 hours and then below 2 Pa. For the secondary drying, the pressure is maintained below 2 Pa and the freeze-dryer shelf temperature is increased from −55° C. to +5° C. at a rate of 0.0625° C. per minute with a 1 h plateau upon reaching every 15° C. increase. Secondary drying is completed by maintaining samples at +5° C. for 4 h at a pressure below 2 Pa. At the end of the freeze-drying process, the glass vials are mechanically sealed. The vacuum is then gently broken and the samples stored at 4° C.

Example 47: Lyophilization of *Neospora hughesi* Tachyzoites Suspended in an Aqueous Formulation Solution of Formulation F1

A suspension of a live attenuated strain of *Neospora hughesi* tachyzoites in a culture medium, freshly egressed from host cells, is centrifuged for 10 min at 1,500 g. The supernatant is removed and the pellet resuspended in an aqueous formulation solution composed of DMEM (i.e. Dulbecco's Modified Eagle Medium) complemented with 0.1M trehalose, 0.1M sucrose, 2.5% autoclaved inulin, 0.1M GSH (glutathione), 1% ectoine, 1% proline, adjusted at pH 7.4 with sodium hydroxide. The concentration of parasites is $1·10^7$/ml. After an equilibration period of 1 h, 1 ml of such a parasite suspension is dispensed in 10 ml glass vials that are placed onto the shelf of a freeze-dryer. Samples are kept freezing at atmospheric pressure for 23 h at a temperature lowered from 20° C. to −75° C. according to a kinetic of −1° C. per minute. The primary drying is performed at −55° C. for 20 h with a pressure maintained between 30 and 80 Pa during the first 7 hours and then below 2 Pa. For the secondary drying, the pressure is maintained below 2 Pa and the freeze-dryer shelf temperature is increased from −55° C. to +5° C. at a rate of 0.0625° C. per minute with a 1 h plateau upon reaching every 15° C. increase. Secondary drying is completed by maintaining samples at +5° C. for 4 h at a pressure below 2 Pa. At the end of the freeze-drying process, the glass vials are mechanically sealed. The vacuum is then gently broken and the samples stored at 4° C.

Example 48: Lyophilization of *Sarcocystis neurona* Bradyzoites Suspended in an Aqueous Formulation Solution of Formulation F1

A suspension of a live attenuated strain of *Sarcocystis neurona* bradyzoites in a culture medium, freshly egressed from host cells, is centrifuged for 10 min at 1,500 g. The supernatant is removed and the pellet resuspended in an aqueous formulation solution composed of DMEM (i.e. Dulbecco's Modified Eagle Medium) complemented with 0.1M trehalose, 0.1M sucrose, 2.5% autoclaved inulin, 0.1M GSH (glutathione), 1% ectoine, 1% proline, adjusted at pH 7.4 with sodium hydroxide. The concentration of parasites is $1·10^7$/ml. After an equilibration period of 1 h, 1 ml of such a parasite suspension is dispensed in 10 ml glass vials that are placed onto the shelf of a freeze-dryer. Samples are kept freezing at atmospheric pressure for 23 h at a temperature lowered from 20° C. to −75° C. according to a kinetic of −1° C. per minute. The primary drying is performed at −55° C. for 20 h with a pressure maintained between 30 and 80 Pa during the first 7 hours and then below 2 Pa. For the secondary drying, the pressure is maintained below 2 Pa and the freeze-dryer shelf temperature is increased from −55° C. to +5° C. at a rate of 0.0625° C. per minute with a 1 h plateau upon reaching every 15° C. increase. Secondary drying is completed by maintaining samples at +5° C. for 4 h at a pressure below 2 Pa. At the end of the freeze-drying process, the glass vials are mechanically sealed. The vacuum is then gently broken and the samples stored at 4° C.

Example 48 Bis: Lyophilization of *Sarcocystis neurona* Merozoites Suspended in an Aqueous Formulation Solution of Formulation F1

A suspension of a live attenuated strain of *Sarcocystis neurona* merozoites in a culture medium, freshly harvested from host cells, is centrifuged for 10 min at 1,500 g. The supernatant is removed and the pellet resuspended in an aqueous formulation solution composed of DMEM (i.e. Dulbecco's Modified Eagle Medium) complemented with 0.1M trehalose, 0.1M sucrose, 2.5% autoclaved inulin, 0.1M GSH (glutathione), 1% ectoine, 1% proline, adjusted at pH 7.4 with sodium hydroxide. The concentration of parasites is $1·10^7$/ml. After an equilibration period of 1 h, 1 ml of such a parasite suspension is dispensed in 10 ml glass vials that are placed onto the shelf of a freeze-dryer. Samples are kept freezing at atmospheric pressure for 23 h at a temperature lowered from 20° C. to −75° C. according to a kinetic of −1° C. per minute. The primary drying is performed at −55° C. for 20 h with a pressure maintained between 30 and 80 Pa during the first 7 hours and then below 2 Pa. For the secondary drying, the pressure is maintained below 2 Pa and the freeze-dryer shelf temperature is increased from −55° C. to +5° C. at a rate of 0.0625° C. per minute with a 1 h plateau upon reaching every 15° C. increase. Secondary drying is completed by maintaining samples at +5° C. for 4 h at a pressure below 2 Pa. At the end of the freeze-drying process, the glass vials are mechanically sealed. The vacuum is then gently broken and the samples stored at 4° C.

Example 49: Lyophilization of *Leishmania donovani* Promastigotes Suspended in an Aqueous Formulation Solution of Formulation F1

A suspension of a live attenuated strain of *Leishmania donovani* promastigotes in a culture medium, is centrifuged for 10 min at 1,500 g. The supernatant is removed and the pellet resuspended in an aqueous formulation solution medium composed of DMEM (i.e. Dulbecco's Modified Eagle Medium) complemented with 0.1M trehalose, 0.1M sucrose, 2.5% autoclaved inulin, 0.1M GSH (glutathione), 1% ectoine, 1% proline, adjusted at pH 7.4 with sodium hydroxide. The concentration of parasites is $1·10^7$/ml. After an equilibration period of 1 h, 1 ml of such a parasite suspension is dispensed in 10 ml glass vials that are placed onto the shelf of a freeze-dryer. Samples are kept freezing at atmospheric pressure for 23 h at a temperature lowered from 20° C. to −75° C. according to a kinetic of −1° C. per minute. The primary drying is performed at −55° C. for 20 h with a pressure maintained between 30 and 80 Pa during the first 7 hours and then below 2 Pa. For the secondary drying, the pressure is maintained below 2 Pa and the freeze-dryer shelf temperature is increased from −55° C. to +5° C. at a rate of 0.0625° C. per minute with a 1 h plateau upon reaching every 15° C. increase. Secondary drying is completed by maintaining samples at +5° C. for 4 h at a pressure below 2 Pa. At the end of the freeze-drying process, the glass vials are mechanically sealed. The vacuum is then gently broken and the samples stored at 4° C.

Example 50: Lyophilization of *Leishmania infantum* Promastigotes Suspended in an Aqueous Formulation Solution of Formulation F1

A suspension of a live attenuated strain of *Leishmania infantum* promastigotes in a culture medium, is centrifuged for 10 min at 1,500 g. The supernatant is removed and the pellet resuspended in an aqueous formulation solution composed of DMEM (i.e. Dulbecco's Modified Eagle Medium) complemented with 0.1M trehalose, 0.1M sucrose, 2.5% autoclaved inulin, 0.1M GSH (glutathione), 1% ectoine, 1% proline, adjusted at pH 7.4 with sodium hydroxide. The concentration of parasites is $1 \cdot 10^7$/ml. After an equilibration period of 1 h, 1 ml of such a parasite suspension is dispensed in 10 ml glass vials that are placed onto the shelf of a freeze-dryer. Samples are kept freezing at atmospheric pressure for 23 h at a temperature lowered from 20° C. to −75° C. according to a kinetic of −1° C. per minute. The primary drying is performed at −55° C. for 20 h with a pressure maintained between 30 and 80 Pa during the first 7 hours and then below 2 Pa. For the secondary drying, the pressure is maintained below 2 Pa and the freeze-dryer shelf temperature is increased from −55° C. to +5° C. at a rate of 0.0625° C. per minute with a 1 h plateau upon reaching every 15° C. increase. Secondary drying is completed by maintaining samples at +5° C. for 4 h at a pressure below 2 Pa. At the end of the freeze-drying process, the glass vials are mechanically sealed. The vacuum is then gently broken and the samples stored at 4° C.

Example 51: Lyophilization of *Plasmodium falciparum* Sporozoites Suspended in an Aqueous Formulation Solution of Formulation F1

A suspension of a live attenuated strain of *Plasmodium falciparum* sporozoites in a culture medium, freshly harvested from host cells, is centrifuged for 10 min at 1,500 g. The supernatant is removed and the pellet resuspended in an aqueous formulation solution composed of DMEM (i.e. Dulbecco's Modified Eagle Medium) complemented with 0.1M trehalose, 0.1M sucrose, 2.5% autoclaved inulin, 0.1M GSH (glutathione), 1% ectoine, 1% proline, adjusted at pH 7.4 with sodium hydroxide. The concentration of parasites is $1 \cdot 10^7$/ml. After an equilibration period of 1 h, 1 ml of such a parasite suspension is dispensed in 10 ml glass vials that are placed onto the shelf of a freeze-dryer. Samples are kept freezing at atmospheric pressure for 23 h at a temperature lowered from 20° C. to −75° C. according to a kinetic of −1° C. per minute. The primary drying is performed at −55° C. for 20 h with a pressure maintained between 30 and 80 Pa during the first 7 hours and then below 2 Pa. For the secondary drying, the pressure is maintained below 2 Pa and the freeze-dryer shelf temperature is increased from −55° C. to +5° C. at a rate of 0.0625° C. per minute with a 1 h plateau upon reaching every 15° C. increase. Secondary drying is completed by maintaining samples at +5° C. for 4 h at a pressure below 2 Pa. At the end of the freeze-drying process, the glass vials are mechanically sealed. The vacuum is then gently broken and the samples stored at 4° C.

Example 51 Bis: Lyophilization of *Plasmodium falciparum* Merozoites Suspended in an Aqueous Formulation Solution of Formulation F1

A suspension of a live attenuated strain of *Plasmodium falciparum* merozoites in a culture medium, freshly harvested from host cells, is centrifuged for 10 min at 1,500 g. The supernatant is removed and the pellet resuspended in an aqueous formulation solution composed of DMEM (i.e. Dulbecco's Modified Eagle Medium) complemented with 0.1M trehalose, 0.1M sucrose, 2.5% autoclaved inulin, 0.1M GSH (glutathione), 1% ectoine, 1% proline, adjusted at pH 7.4 with sodium hydroxide. The concentration of parasites is $1 \cdot 10^7$/ml. After an equilibration period of 1 h, 1 ml of such a parasite suspension is dispensed in 10 ml glass vials that are placed onto the shelf of a freeze-dryer. Samples are kept freezing at atmospheric pressure for 23 h at a temperature lowered from 20° C. to −75° C. according to a kinetic of −1° C. per minute. The primary drying is performed at −55° C. for 20 h with a pressure maintained between 30 and 80 Pa during the first 7 hours and then below 2 Pa. For the secondary drying, the pressure is maintained below 2 Pa and the freeze-dryer shelf temperature is increased from −55° C. to +5° C. at a rate of 0.0625° C. per minute with a 1 h plateau upon reaching every 15° C. increase. Secondary drying is completed by maintaining samples at +5° C. for 4 h at a pressure below 2 Pa. At the end of the freeze-drying process, the glass vials are mechanically sealed. The vacuum is then gently broken and the samples stored at 4° C.

Example 52: Lyophilization of *Plasmodium vivax* Sporozoites Suspended in an Aqueous Formulation Solution of Formulation F1

A suspension of a live attenuated strain of *Plasmodium vivax* sporozoites in a culture medium, freshly harvested from host cells, is centrifuged for 10 min at 1,500 g. The supernatant is removed and the pellet resuspended in an aqueous formulation solution composed of DMEM (i.e. Dulbecco's Modified Eagle Medium) complemented with 0.1M trehalose, 0.1M sucrose, 2.5% autoclaved inulin, 0.1M GSH (glutathione), 1% ectoine, 1% proline, adjusted at pH 7.4 with sodium hydroxide. The concentration of parasites is $1 \cdot 10^7$/ml. After an equilibration period of 1 h, 1 ml of such a parasite suspension is dispensed in 10 ml glass vials that are placed onto the shelf of a freeze-dryer. Samples are kept freezing at atmospheric pressure for 23 h at a temperature lowered from 20° C. to −75° C. according to a kinetic of −1° C. per minute. The primary drying is performed at −55° C. for 20 h with a pressure maintained between 30 and 80 Pa during the first 7 hours and then below 2 Pa. For the secondary drying, the pressure is maintained below 2 Pa and the freeze-dryer shelf temperature is increased from −55° C. to +5° C. at a rate of 0.0625° C. per minute with a 1 h plateau upon reaching every 15° C. increase. Secondary drying is completed by maintaining samples at +5° C. for 4 h at a pressure below 2 Pa. At the end of the freeze-drying process, the glass vials are mechanically sealed. The vacuum is then gently broken and the samples stored at 4° C.

Example 52 Bis: Lyophilization of *Plasmodium vivax* Merozoites Suspended in an Aqueous Formulation Solution of Formulation F1

A suspension of a live attenuated strain of *Plasmodium vivax* merozoites in a culture medium, freshly harvested from host cells, is centrifuged for 10 min at 1,500 g. The supernatant is removed and the pellet resuspended in an aqueous formulation solution composed of DMEM (i.e. Dulbecco's Modified Eagle Medium) complemented with 0.1M trehalose, 0.1M sucrose, 2.5% autoclaved inulin, 0.1M GSH (glutathione), 1% ectoine, 1% proline, adjusted at pH 7.4 with sodium hydroxide. The concentration of parasites is $1 \cdot 10^7$/ml. After an equilibration period of 1 h, 1 ml of such a parasite suspension is dispensed in 10 ml glass vials that are placed onto the shelf of a freeze-dryer. Samples are kept freezing at atmospheric pressure for 23 h at a temperature lowered from 20° C. to −75° C. according to a kinetic of −1° C. per minute. The primary drying is performed at −55° C. for 20 h with a pressure maintained between 30 and 80 Pa during the first 7 hours and then below 2 Pa. For the secondary drying, the pressure is maintained below 2 Pa and the freeze-dryer shelf temperature is increased from −55° C. to +5° C. at a rate of 0.0625° C. per minute with a 1 h plateau upon reaching every 15° C. increase. Secondary drying is completed by maintaining samples at +5° C. for 4 h at a pressure below 2 Pa. At the end of the freeze-drying process, the glass vials are mechanically sealed. The vacuum is then gently broken and the samples stored at 4° C.

Having thus described in detail preferred embodiments of the present invention, it is to be understood that the invention defined by the appended claims is not to be limited by particular details set forth in the above description as many apparent variations thereof are possible without departing from the spirit or scope thereof.

What is claimed:

1. A lyophilized composition containing freeze-dried protozoa of intracellular nature, wherein said lyophilized composition is devoid of protozoal host cells and contains a moisture content ranging between about 1% to 12% by weight, wherein said protozoa comprise live attenuated strains of *Toxoplasma* parasites, wherein said lyophilized composition further comprises a cryoprotectant, and wherein said cryoprotectant is present in an effective amount to maintain the ability of more than 1% of said freeze-dried protozoa to be restored to a viable state by reconstitution of the lyophilized composition, and wherein said restored protozoa maintain the ability to vaccinate and effectively protect against *Toxoplasma* parasite infections.

2. The lyophilized composition of claim 1, wherein said freeze-dried protozoa are protozoa of fragile state.

3. The lyophilized composition of claim 1, wherein said freeze-dried protozoa have immunogenic and/or prophylactic activity upon reconstitution.

4. A process for reconstituting the lyophilized composition of claim 1, comprising adding a rehydration medium to said lyophilized composition, whereby more than 1% of said freeze-dried protozoa are restored to a viable state and maintain the ability to vaccinate and effectively protect against *Toxoplasma* parasite infections.

5. The process of claim 4, wherein the rehydration medium is added at a rate ranging from 25 μL per second to 1000 μL per second.

6. The lyophilized composition of claim 1, wherein the lyophilized composition has been stored at a temperature from −25° C. to 25° C. for longer than two weeks.

7. The lyophilized composition of claim 6, wherein the lyophilized composition has been stored at a temperature from −25° C. to 2° C.

8. The lyophilized composition of claim 6, wherein the lyophilized composition has been stored at a temperature 2° C. to 8° C.

9. The lyophilized composition of claim 6, wherein the lyophilized composition has been stored at a temperature from 8° C. to 25° C.

10. The lyophilized composition of claim 2, wherein said freeze-dried protozoa are in a tachyzoite state, a bradyzoite state, a sporozoite state, a merozoite state, or any combinations thereof.

11. The lyophilized composition of claim 1, wherein said cryoprotectant is selected from DMSO, a monosaccharide, a disaccharide, an oligosaccharide, a polysaccharide, or any combinations thereof.

12. The lyophilized composition of claim 11, wherein the cryoprotectant is sucrose, trehalose, glucose, inulin, or any combinations thereof.

13. The lyophilized composition of claim 11, further comprising an osmoprotectant.

14. The lyophilized composition of claim 13, wherein said osmoprotectant is ectoine.

15. The lyophilized composition of claim 11, further comprising an antioxidant selected from glutathione (GSH), epigallocatechin gallate (EGCG), ascorbic acid, or any combinations thereof.

16. The lyophilized composition of claim 11, further comprising proline.

17. The process of claim 4, wherein the rehydration medium is Dulbecco's Modified Eagle Medium (DMEM).

18. The process of claim 4, wherein the rehydration medium is added at a rate of 250 μL per second.

19. The lyophilized composition of claim 1, wherein the protozoa are tachyzoites.

20. The lyophilized composition of claim 1, wherein the lyophilized composition contains a moisture content ranging between about 4% to 12% by weight.

21. A process for obtaining the lyophilized composition of claim 1, comprising:

a step of primary drying of a frozen suspension comprising live attenuated strains of *Toxoplasma* parasites par to obtain a primary dried composition, wherein said step of primary drying is carried out at about −55° C., for about 20 h and wherein said step of primary drying is carried out at a pressure comprised from about 30 to about 80 Pa, for 0 to 7 h, and then at a pressure below 2 Pa for the remaining time, and a step of secondary drying of the primary dried composition to obtain a lyophilized composition with a moisture content of about 1% to 12% by weight, wherein said step of secondary drying is carried out at a pressure below 2 Pa and at a temperature increasing from −55° C. to +5° C. at a rate comprised from about 0.01° C./min to about 0.2° C./min, and wherein said secondary drying comprises a temperature plateau of 1 h at every increase of 15° C., and wherein said temperature being maintained at +5° C. for 4 h when reaching said temperature.

22. The process of claim 21, wherein the frozen suspension is obtained by freezing a suspension of protozoa for 4 to 23 h, at atmospheric pressure, by lowering the initial temperature of the suspension of protozoa to a temperature comprised from about −40° C. to about −80° C. from an initial temperature of the suspension of protozoa being comprised from about 15° C. to about 25° C., and wherein said lowering of the temperature is carried out at a rate comprised from about −0.1° C./min to about −10° C./min.

23. The process of claim 21, further comprising an initial step of suspending protozoa in an aqueous formulation solution comprising a culture medium of said protozoa and at least one cryoprotectant, wherein said aqueous formulation solution further comprises at least one osmoprotectant and/or at least one antioxidant and/or at least one other additive, and wherein the culture medium in said aqueous formulation solution is DMEM, RPMI or PBS, the cryoprotectant in said formulation solution is selected from the group comprising DMSO, a monosaccharide, a disaccharide, an oligosaccharide, a polysaccharide, sucrose, trehalose, glucose, inulin or a mixture thereof, the osmoprotectant in said formulation solution is ectoine, the antioxidant in said formulation solution is selected from the group comprising GSH, EGCG, ascorbic acid or a mixture thereof, and the other additive in said formulation solution is selected from polymers, copolymers, amino-acids, in particular L-proline, peptides, proteins or a mixture thereof.

24. The process of claim 23, wherein said aqueous formulation solution comprises:
   a culture medium selected from DMEM, RPMI, or PBS
   0 mM to about 3000 mM DMSO,
   0 mM to about 300 mM sucrose,
   0 mM to about 1000 mM trehalose,
   0 mM to about 400 mM (fructose equivalent) inulin,
   0 mM to about 400 mM ascorbic acid,
   0 mM to about 10 mM EGCG,
   0 mM to about 200 mM GSH,
   0 mM to about 150 mM proline,
   0 mM to about 150 mM ectoine,
provided that the concentration of at least one of the components among DMSO, sucrose, trehalose, inulin, ascorbic acid, EGCG, GSH, proline or ectoine is greater than 0 mM; and wherein the solution is adjusted at pH 7.4 with sodium hydroxide.

* * * * *